US010522247B2

(12) United States Patent
Galley et al.

(10) Patent No.: US 10,522,247 B2
(45) Date of Patent: Dec. 31, 2019

(54) METHODS OF ASSESSING DIABETES TREATMENT PROTOCOLS BASED ON PROTOCOL COMPLEXITY LEVELS AND PATIENT PROFICIENCY LEVELS

(71) Applicant: Roche Diabetes Care, Inc., Indianapolis, IN (US)

(72) Inventors: Paul J. Galley, Cumberland, IN (US); Stefan Weinert, Pendleton, IN (US); David Hasker, San Jose, CA (US); Ulrich Porsch, Weinheim (DE)

( * ) Notice: Subject to any disclaimer, the term of this patent is extended or adjusted under 35 U.S.C. 154(b) by 361 days.

(21) Appl. No.: 15/270,385

(22) Filed: Sep. 20, 2016

(65) Prior Publication Data

US 2017/0011176 A1    Jan. 12, 2017

Related U.S. Application Data

(62) Division of application No. 12/980,652, filed on Dec. 29, 2010, now abandoned.

(51) Int. Cl.
*G16H 20/10* (2018.01)
*G06Q 10/06* (2012.01)

(52) U.S. Cl.
CPC ..... *G16H 20/10* (2018.01); *G06Q 10/063112* (2013.01)

(58) Field of Classification Search
CPC .................................................. G16H 20/10
See application file for complete search history.

(56) References Cited

U.S. PATENT DOCUMENTS

| 4,151,845 A | 5/1979 | Clemens |
| 4,731,726 A | 3/1988 | Allen, III |
| 4,803,625 A | 2/1989 | Fu et al. |
| 5,364,346 A | 11/1994 | Schrezenmeir |
| 5,377,258 A | 12/1994 | Bro |
| 5,572,421 A | 11/1996 | Altman et al. |
| 5,576,952 A | 11/1996 | Stutman et al. |
| 5,665,065 A | 9/1997 | Colman et al. |
| 5,722,418 A | 3/1998 | Bro |
| 5,822,715 A | 10/1998 | Worthington et al. |
| 5,840,020 A | 11/1998 | Heinonen et al. |
| 5,868,669 A | 2/1999 | Iliff |
| 5,879,163 A | 3/1999 | Brown et al. |

(Continued)

FOREIGN PATENT DOCUMENTS

DE  102005041627 A1   3/2007
EP       1702559 A2   9/2006

(Continued)

OTHER PUBLICATIONS

Accu-Chek Spirit Pump User Guide, Sep. 2008, pp. 1-201.

(Continued)

*Primary Examiner* — Soren Harward
(74) *Attorney, Agent, or Firm* — Dinsmore & Shohl, LLP

(57) ABSTRACT

Embodiments of methods of assessing a diabetes treatment protocol comprise determining a protocol complexity level corresponding to a degree of difficulty of completing the diabetes treatment protocol by utilizing the processor, determining a patient proficiency level corresponding to a skill set of the patient in conducting the diabetes treatment protocol by utilizing the processor, comparing the protocol complexity level to the patient proficiency level via the processor, and providing an output based on the comparison.

29 Claims, 8 Drawing Sheets

(56) References Cited

U.S. PATENT DOCUMENTS

| | | |
|---|---|---|
| 5,897,493 A | 4/1999 | Brown |
| 5,971,922 A | 10/1999 | Arita et al. |
| 6,018,713 A | 1/2000 | Coli et al. |
| 6,024,699 A | 2/2000 | Surwit |
| 6,039,688 A | 3/2000 | Douglas et al. |
| 6,108,665 A | 8/2000 | Bair et al. |
| 6,234,964 B1 | 5/2001 | Iliff |
| 6,241,633 B1 | 6/2001 | Conroy |
| 6,269,314 B1 | 7/2001 | Itawaki et al. |
| 6,326,160 B1 | 12/2001 | Dunn et al. |
| 6,338,039 B1 | 1/2002 | Lonski et al. |
| 6,352,505 B1 | 3/2002 | Bortz |
| 6,379,301 B1 | 4/2002 | Worthington et al. |
| 6,424,847 B1 | 7/2002 | Mastrototaro et al. |
| 6,425,863 B1 | 7/2002 | Werner et al. |
| 6,544,212 B2 | 4/2003 | Galley et al. |
| 6,567,785 B2 | 5/2003 | Clendenon |
| 6,575,900 B1 | 6/2003 | Zweig et al. |
| 6,645,368 B1 | 11/2003 | Beaty et al. |
| 6,656,114 B1 | 12/2003 | Poulsen et al. |
| 6,691,043 B2 | 2/2004 | Ribeiro, Jr. |
| 6,770,029 B2 | 8/2004 | Iliff |
| 6,835,175 B1 | 12/2004 | Porumbescu |
| 6,879,970 B2 | 4/2005 | Shiffman et al. |
| 6,923,763 B1 | 8/2005 | Kovatchev et al. |
| 6,954,662 B2 | 10/2005 | Freger et al. |
| 7,179,226 B2 | 2/2007 | Crothall et al. |
| 7,229,430 B2 | 6/2007 | Hickle et al. |
| 7,241,265 B2 | 7/2007 | Cummings et al. |
| 7,266,400 B2 | 9/2007 | Fine et al. |
| 7,278,983 B2 | 10/2007 | Ireland et al. |
| 7,381,523 B2 | 6/2008 | Efendic |
| 7,389,133 B1 | 6/2008 | Kotulla et al. |
| 7,404,796 B2 | 7/2008 | Ginsberg |
| 7,405,196 B2 | 7/2008 | Rosskamp et al. |
| 7,413,749 B2 | 8/2008 | Wright et al. |
| 7,415,447 B2 | 8/2008 | Shiffman et al. |
| 7,509,156 B2 | 3/2009 | Flanders |
| 7,523,040 B2 | 4/2009 | Kirchhoff et al. |
| 7,553,281 B2 | 6/2009 | Hellwig et al. |
| 7,676,329 B2 | 3/2010 | Garczarek et al. |
| 7,685,000 B1 | 3/2010 | Petit et al. |
| 7,734,323 B2 | 6/2010 | Blomquist et al. |
| 7,761,310 B2 | 7/2010 | Rodgers |
| 7,766,830 B2 | 8/2010 | Fox et al. |
| 8,078,592 B2 | 12/2011 | Gejdos et al. |
| 8,117,020 B2 | 2/2012 | Abensour et al. |
| 2002/0019752 A1 | 2/2002 | Takase |
| 2002/0107476 A1 | 8/2002 | Mann et al. |
| 2002/0143563 A1 | 10/2002 | Hufford et al. |
| 2002/0161288 A1 | 10/2002 | Shin et al. |
| 2003/0028399 A1 | 2/2003 | Davis et al. |
| 2003/0104982 A1 | 6/2003 | Wittmann et al. |
| 2003/0130616 A1 | 7/2003 | Steil et al. |
| 2003/0208113 A1 | 11/2003 | Mault et al. |
| 2003/0211617 A1 | 11/2003 | Jones |
| 2004/0078065 A1 | 4/2004 | Kroll |
| 2004/0122701 A1 | 6/2004 | Dahlin et al. |
| 2004/0122709 A1 | 6/2004 | Avinash et al. |
| 2004/0243443 A1 | 12/2004 | Asano et al. |
| 2004/0247748 A1 | 12/2004 | Bronkema |
| 2005/0010416 A1 | 1/2005 | Anderson et al. |
| 2005/0016844 A1 | 1/2005 | Burke et al. |
| 2005/0020903 A1 | 1/2005 | Krishnan et al. |
| 2005/0021372 A1 | 1/2005 | Mikkelsen et al. |
| 2005/0049179 A1 | 3/2005 | Davidson et al. |
| 2005/0075553 A1 | 4/2005 | Sakai et al. |
| 2005/0119540 A1 | 6/2005 | Potts et al. |
| 2005/0119788 A1 | 6/2005 | Engleson et al. |
| 2006/0010014 A1 | 1/2006 | Brown |
| 2006/0010098 A1 | 1/2006 | Goodnow et al. |
| 2006/0025931 A1 | 2/2006 | Rosen et al. |
| 2006/0030890 A1 | 2/2006 | Cosentino et al. |
| 2006/0031094 A1 | 2/2006 | Cohen et al. |
| 2006/0171503 A1 | 8/2006 | O'Hara et al. |
| 2006/0173406 A1 | 8/2006 | Hayes et al. |
| 2006/0195022 A1 | 8/2006 | Trepagnier et al. |
| 2006/0195029 A1 | 8/2006 | Shults et al. |
| 2006/0195342 A1 | 8/2006 | Khan et al. |
| 2006/0253296 A1 | 11/2006 | Liisberg et al. |
| 2006/0271404 A1 | 11/2006 | Brown |
| 2006/0287883 A1 | 12/2006 | Turgiss et al. |
| 2007/0048691 A1 | 3/2007 | Brown |
| 2007/0055483 A1 | 3/2007 | Lee et al. |
| 2007/0100659 A1 | 5/2007 | Preiss |
| 2007/0106135 A1 | 5/2007 | Sloan et al. |
| 2007/0116329 A1 | 5/2007 | Tsubata |
| 2007/0162304 A1 | 7/2007 | Rodgers |
| 2007/0198296 A1 | 8/2007 | Pellinat et al. |
| 2007/0213604 A1 | 9/2007 | Brown |
| 2007/0253904 A1 | 11/2007 | Gunton et al. |
| 2007/0282636 A1 | 12/2007 | Sauk et al. |
| 2008/0025591 A1 | 1/2008 | Bhanot et al. |
| 2008/0109043 A1 | 5/2008 | Salo et al. |
| 2008/0125636 A1 | 5/2008 | Ward et al. |
| 2008/0146895 A1 | 6/2008 | Olson et al. |
| 2008/0154513 A1 | 6/2008 | Kovatchev et al. |
| 2008/0172027 A1 | 7/2008 | Blomquist |
| 2008/0177119 A1 | 7/2008 | Juttu et al. |
| 2008/0177149 A1 | 7/2008 | Weinert et al. |
| 2008/0177165 A1 | 7/2008 | Blomquist et al. |
| 2008/0183494 A1 | 7/2008 | Cuddihy et al. |
| 2008/0201325 A1 | 8/2008 | Doniger et al. |
| 2008/0206799 A1 | 8/2008 | Blomquist |
| 2008/0214919 A1 | 9/2008 | Harmon et al. |
| 2008/0228056 A1 | 9/2008 | Blomquist et al. |
| 2008/0234943 A1 | 9/2008 | Ray et al. |
| 2008/0234992 A1 | 9/2008 | Ray et al. |
| 2008/0243902 A1 | 10/2008 | Rong et al. |
| 2008/0255438 A1 | 10/2008 | Saidara et al. |
| 2008/0262745 A1 | 10/2008 | Polidori |
| 2008/0269585 A1 | 10/2008 | Ginsberg |
| 2008/0306353 A1 | 12/2008 | Douglas et al. |
| 2008/0319384 A1 | 12/2008 | Yodfat et al. |
| 2009/0000606 A1 | 1/2009 | Thukral et al. |
| 2009/0018406 A1 | 1/2009 | Yodfat et al. |
| 2009/0150177 A1 | 6/2009 | Buck et al. |
| 2009/0150186 A1 | 6/2009 | Cohen et al. |
| 2009/0164239 A1 | 6/2009 | Hayter et al. |
| 2009/0176692 A1 | 7/2009 | Habermann et al. |
| 2009/0177147 A1 | 7/2009 | Blomquist et al. |
| 2009/0234262 A1 | 9/2009 | Reid et al. |
| 2009/0240520 A1 | 9/2009 | Takano et al. |
| 2009/0247836 A1 | 10/2009 | Cole et al. |
| 2009/0253970 A1 | 10/2009 | Bashan et al. |
| 2009/0253973 A1 | 10/2009 | Bashan et al. |
| 2009/0281393 A1 | 11/2009 | Smith |
| 2010/0016700 A1 | 1/2010 | Sieh et al. |
| 2010/0138197 A1 | 6/2010 | Sher |
| 2010/0141656 A1 | 6/2010 | Krieftewirth |
| 2010/0160757 A1 | 6/2010 | Weinert et al. |
| 2010/0174553 A1 | 7/2010 | Kaufman et al. |
| 2010/0184565 A1 | 7/2010 | Avellino |
| 2010/0198142 A1 | 8/2010 | Sloan et al. |
| 2010/0198520 A1 | 8/2010 | Breton et al. |
| 2010/0222765 A1 | 9/2010 | Blomquist et al. |
| 2010/0262434 A1 | 10/2010 | Shaya |
| 2010/0265073 A1 | 10/2010 | Harper |
| 2010/0274497 A1 | 10/2010 | Rush |
| 2010/0330598 A1 | 12/2010 | Thukral et al. |
| 2010/0331650 A1 | 12/2010 | Batman et al. |
| 2010/0331651 A1 | 12/2010 | Groll |
| 2011/0015511 A1 | 1/2011 | Bousamra et al. |
| 2011/0071365 A1 | 3/2011 | Lee et al. |
| 2012/0226117 A1 | 9/2012 | Lamego et al. |

FOREIGN PATENT DOCUMENTS

| | | |
|---|---|---|
| EP | 1728469 A2 | 12/2006 |
| EP | 1956508 A2 | 8/2008 |
| EP | 2006786 A1 | 12/2008 |
| FR | 2760962 A1 | 3/1997 |
| JP | 2002175372 A | 6/2002 |
| JP | 2005011329 A | 1/2005 |

(56) References Cited

FOREIGN PATENT DOCUMENTS

| | | |
|---|---|---|
| JP | 2005110920 A | 4/2005 |
| JP | 2007143623 A | 6/2007 |
| WO | 94/20916 A1 | 9/1994 |
| WO | 9901836 | 1/1999 |
| WO | 0009007 | 2/2000 |
| WO | 0122343 A2 | 3/2001 |
| WO | 0133314 A2 | 5/2001 |
| WO | 01/52727 A1 | 7/2001 |
| WO | 2003002258 A1 | 1/2003 |
| WO | 2003046695 A2 | 6/2003 |
| WO | 2003082096 A1 | 10/2003 |
| WO | 2004015539 A2 | 2/2004 |
| WO | 2004/084820 A2 | 10/2004 |
| WO | 2004114184 A1 | 12/2004 |
| WO | 2007081853 A2 | 7/2007 |
| WO | 2007117719 A2 | 10/2007 |
| WO | 2007/149319 A2 | 12/2007 |
| WO | 2007144419 A2 | 12/2007 |
| WO | 2008/091320 A2 | 7/2008 |
| WO | 2008/105859 A1 | 9/2008 |
| WO | 2008/131324 A1 | 10/2008 |
| WO | 2009/009528 A1 | 1/2009 |
| WO | 2009/013637 A2 | 1/2009 |
| WO | 2009/075925 A1 | 6/2009 |
| WO | 2009/146119 A2 | 12/2009 |
| WO | 2010000266 A1 | 1/2010 |
| WO | 2010/039743 A1 | 4/2010 |
| WO | 2010/072386 A2 | 7/2010 |
| WO | 2010/075350 A1 | 7/2010 |
| WO | 2010072387 A2 | 7/2010 |
| WO | 2010/089304 A1 | 8/2010 |
| WO | 2010/089305 A1 | 8/2010 |
| WO | 2010/089306 A1 | 8/2010 |
| WO | 2010/089307 A1 | 8/2010 |
| WO | 2010/097796 A1 | 9/2010 |

OTHER PUBLICATIONS

Accu-Chek Pocket Compass Software with Bolus Calculator User Guide, Oct. 2005, pp. 1-174.
Accu-Chek Aviva Blood Glucose Meter Owner's Booklet, Sep. 2008, pp. 1-92.
Accu-Chek 360 Diabetes Management System, Aug. 24, 2010, pp. 1-2.
Accu-Chek Smart Pix Device Reader User's Manual, Sep. 2008, pp. 1-92.
De Groen, et al., "Applying World Wide Web Technology to the Study of Patients with Rare Diseases, Annals of Internal Medicine", vol. 129, No. 2, Jul. 15, 1998, pp. 107-113, XP002587966, 1998.
Dassau, et al., "Detection of a Meal Using Continuous Glucose Monitoring", Diabetes Care, vol. 31, No. 2, Feb. 2008, pp. 295-300.
Gerstein et al., "A randomized trial of adding insulin glargine vs. avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperclycaemia Treatment) Study", Diabetic Medicine, vol. 23, pp. 736-742, 2006.
Hirsch et al., "A Real-World Approach to Insulin Therapy in Primary Care Practice", Practical Pointers, Clinical Diabetes, vol. 23, Nov. 2, 2005.
Nathan, et al., "Medical Management of Hyperglycemia in Type 2 Diabetes: A Consensus Algorithm for the Initiation and Adjustment of Therapy", Diabetes Care, vol. 31, No. 12: pp. 1-11, Dec. 2008.
Riddle, et al., "The Treat-to-Target Trial, Randomized addition of glargine or human NPH insulin to oral therapy of type 2 diabetic patients", Diabetes Care, vol. 26, No. 11: pp. 2080-3086, Nov. 2003.
Crowe, et al., "Time Synching or Time Sinking?", Diabetes Technology & Therapeutics, vol. 7, No. 5, 2005.
Munro, et al., "Association Between Medication Regimen Complexity and Achievement of Therapeutic Goals in Patients with Type 2 Diabetes", School of Pharmacy, The Robert Gordon University, Aberdeen, AB10 1 FR (k.munroe@rgu.ac.uk), pp. 1, 2.
Ingersoll, et al., "The Impact of Medication Regimen Factors on Adherence to Chronic Treatment: a Review of Literature", NIH Public Access, Author Manuscript, J Behav Med. Jun. 2008; 31(3): 213-224. doi:10.1007/s10865-007-9147-y; pp. 1-16.
Pollack, et al., "Impact of treatment Complexity on Adherence and Glycemic Control: An Analysis of Oral Antidiabetic Agents", www.jcomjournal.com, vol. 17, No. 6, Jun. 2010, pp. 257-265.
Joslin Diabetes Center & Joslin Clinic, "Clinical Guideline for Pharmacological Management of Type 2 Diabetes", Jan. 12, 2007, pp. 1-9.
Joslin Diabetes Center & Joslin Clinic, "Clinical Guideline for Adults with Diabetes", May 21, 2010, pp. 1-13.
International Search Report, Application No. PCT/EP2009/009170 filed Dec. 21, 2009, completion of ISR is Sep. 24, 2010, pp. 1-24.
International Search Report, Application No. PCT/EP2009/009171 filed Dec. 21, 2009, completion of ISR is Jun. 21, 2010, pp. 1-14.
Breton, M. et al.; Analysis, Modeling, and Simulation of the Accuracy of Continuous Glucose Sensors; Journal of Diabetes Science and Technology; Sep. 2008; pp. 853-862; vol. 2, Issue 5; Diabetes Technology Society.
Huang Elbert S., "The key to preventing burnout: understanding the burden of diabetes treatment", DiabetesVoice, 53, Issue 3, pp. 33-35, Dec. 2008.
Larimer, et al., "Relapse Prevention, an Overview of Marlatt's Cognitive-Behavioral Model", Alcohol Research & vol. 23, No. 2, pp. 151-160, 1999.
Marlatt, et al., "Clinical Guidelines for Implementing Relapse Prevention Therapy", Addictive Behaviors Research Center/ University of Washington, pp. 1-49, Dec. 2002.
Montani et al., "Integrating Case Based and Rule Based Reasoning in a Decision Support System: Evalution with Simulated Patients", AMIA, Inc., pp. 887-891, 1999.
Montani et al., "Managing diabetic patients through a Multi Modal Reasoning methodology", International Journal of Medical Informatics, vol. 58, Complete, pp. 243-256, Sep. 1, 2000.
Schmidt et al., "Case-based Reasoning for Medical Knowledge-based Systems", Institute for Medical Informatics and Biometry, University of Rostock Rembrandstr. 16/17, D-18055 Rostock, Germany, 2000.
Denis Raccah, "Insulin therapy in patients with type 2 diabetes mellitus: Treatment to target fasting and postprandial blood glucose levels", Insulin 1:158-165, 2006.
Morgan et al., "Uncertainty A Guide to Dealing with Uncertainty in Quantitative Risk and Poly Analysis", Cambridge University Press, pp. 307-310, 1990.
Brand et al., "Updating uncertainty in an integrated risk assessment: Conceptual framework and methods", Risk Analysis 1995 US, vol. 15, No. 6, pp. 719-731, 1995.
Lustria, et al., Computer-Tailored Health Interventions Delivered Over the Web: Review and Analysis of Key Components, U.S. National Library of Medicine, National Institute of Health, 2009, p. 1.
Office Action dated Apr. 19, 2018 pertaining to U.S. Appl. No. 14/252,052, 38 pages.

| 237a | 240a | 256a | 12/23/2009 8:00 | 1 | |
| 237b | 240b | 256b | 12/23/2009 9:00 | 2 | 5,1 |
| 237c | 240c | 256c | 12/23/2009 9:30 | 3 | 5,1 |
| 237d | 240d | 256d | 12/23/2009 10:00 | <null> | |
| ... | ... | ... | ... | ... | |
| 237n | 240n | 256n | mm/dd/yyyy hh:mm | n | |

FIG. 4

METHODS OF ASSESSING DIABETES TREATMENT PROTOCOLS BASED ON PROTOCOL COMPLEXITY LEVELS AND PATIENT PROFICIENCY LEVELS

CROSS-REFERENCE TO RELATED APPLICATIONS

This application is division of U.S. patent application Ser. No. 12/980,652 filed Dec. 29, 2010, now abandoned, which application is incorporated herein by reference in its entirety.

TECHNICAL FIELD

Embodiments of the present disclosure relate generally to diabetes management, and specifically relate to methods of assessing a diabetes treatment protocol to align the skill set of a patient with the complexity of the diabetes treatment protocol.

BACKGROUND

A disease which is long lasting or which reoccurs often is defined typically as a chronic disease. Known chronic diseases include, among others, depression, compulsive obsession disorder, alcoholism, asthma, autoimmune diseases (e.g., ulcerative colitis, lupus erythematosus), osteoporosis, cancer, and diabetes mellitus. Such chronic diseases require chronic care management for effective long-term treatment.

In the example of diabetes mellitus, which is characterized by hyperglycemia resulting from inadequate insulin secretion, insulin action, or both, it is known that diabetes manifests itself differently in each person because of each person's unique physiology that interacts with variable health and lifestyle factors such as diet, weight, stress, illness, sleep, exercise, and medication intake.

Biomarkers are patient biologically derived indicators of biological or pathogenic processes, pharmacologic responses, events or conditions (e.g., aging, disease or illness risk, presence or progression, etc.). For example, a biomarker can be an objective measurement of a variable related to a disease, which may serve as an indicator or predictor of that disease. In the case of diabetes mellitus, such biomarkers include measured values for glucose, lipids, triglycerides, and the like. A biomarker can also be a set of parameters from which to infer the presence or risk of a disease, rather than a measured value of the disease itself. When properly collected and evaluated, biomarkers can provide useful information related to a medical question about the patient, as well as be used as part of a medical assessment, as a medical control, and/or for medical optimization.

For diabetes, clinicians generally treat diabetic persons according to published therapeutic guidelines such as, for example, Joslin Diabetes Center & Joslin Clinic, *Clinical Guideline for Pharmacological Management of Type 2 Diabetes* (2007) and Joslin Diabetes Center & Joslin Clinic, *Clinical Guideline for Adults with Diabetes* (2008). The guidelines may specify a desired biomarker value, e.g., a fasting blood glucose value of less than 100 mg/dl, or the clinician can specify a desired biomarker value based on the clinician's training and experience in treating patients with diabetes.

While the development of a suitable diabetes treatment protocol or treatment regimen is important, the success of a diabetes treatment protocol is dependent on the patient or patient's adherence to the diabetes treatment protocol. However, adherence may be prevented when the diabetes treatment protocol or the tasks of the diabetes treatment protocol are too complex for the patient. Specifically, a patient may lack the required skill set to perform tasks of the diabetes treatment protocol (e.g., collecting biomarker readings). Moreover, the patient may be unaware that they lack the required skill set to perform the diabetes treatment protocol.

It is desirable to provide a method of tailoring a diabetes treatment protocol to a patient skill set by providing additional upfront and ongoing assistance specific for patients who have not yet demonstrated proficiency for a diabetes treatment protocol.

SUMMARY

Embodiments of the present disclosure are directed to improving adherence of a protocol by tailoring the complexity of a diabetes treatment protocol to the skill set of a patent. It is understood that adherence to a protocol is improved when the goals are agreed upon, the steps are understood and the patient possesses the appropriate materials and skills to complete the subtasks. Consequently, the present embodiments compare the skill set of a patient (patient proficiency level) with the complexity of the diabetes treatment protocol. Additionally, the embodiments of the present invention may benefit the patient or healthcare provider by informing the patient of a complexity level of a diabetes treatment protocol, and a patient's proficiency level in relation to the diabetes treatment protocol.

In one embodiment, a method of assessing a diabetes treatment protocol by utilizing a processor is provided. The method comprises determining a protocol complexity level corresponding to a degree of difficulty of completing the diabetes treatment protocol by utilizing the processor, determining a patient proficiency level corresponding to a skill set of the patient in conducting the diabetes treatment protocol by utilizing the processor, comparing the protocol complexity level to the patient proficiency level, wherein the comparison is performed by the processor, and providing an output based on the comparison.

According to another embodiment, a collection device for assessing a diabetes treatment protocol is provided. The collection device comprises a meter configured to measure one or more selected biomarkers, a processor disposed inside the meter and coupled to memory, software having instructions that when executed by the processor causes the processor to compute a protocol complexity level corresponding to a degree of difficulty of completing the diabetes treatment protocol, compute a patient proficiency level corresponding to a skill set of the patient in conducting the diabetes treatment protocol, and compare the patient proficiency level and the protocol complexity level. The collection device further comprises a display unit configured to provide the results of the comparison.

According to yet another embodiment, a method of calculating a protocol complexity level for a diabetes treatment protocol by utilizing a processor is provided, wherein the processor is programmed with calculation instructions for the protocol complexity level which corresponds to a degree of difficulty of completing the diabetes treatment protocol. The method comprises selecting a calculation methodology for the protocol complexity level utilizing the processor, wherein the processor selects the calculation methodology appropriate for the diabetes treatment protocol by executing the programmed calculation instructions. The selected calculation methodology may utilize predefined protocol complexity values associated with known diabetes treatment protocols, task complexity values which are assigned to one or more tasks of the diabetes treatment protocol, or combinations thereof. The method further comprises computing the protocol complexity level of the diabetes treatment protocol using the selected calculation methodology.

In yet another embodiment, a method of calculating a patient proficiency level for a diabetes treatment protocol is provided, wherein the method utilizes a processor, the processor being programmed with calculation instructions for the patient proficiency level. The method comprises selecting a calculation methodology for the patient proficiency level via the processor, wherein the processor selects the calculation methodology appropriate for the diabetes treatment protocol by executing the programmed calculation instructions. The selected calculation methodology utilizes predefined patient proficiency levels, prior patient proficiency levels calculated based on stored data of previously performed treatment protocol or any tasks of the treatment protocol, or combinations thereof; and computing the patient proficiency level for the diabetes treatment protocol based on the selected calculation methodology.

These and other advantages and features of the invention disclosed herein, will be made more apparent from the description, drawings and claims that follow.

BRIEF DESCRIPTION OF THE DRAWINGS

The following detailed description of the embodiments of the present invention can be best understood when read in conjunction with the following drawings, where like structure is indicated with like reference numerals.

FIG. 4 shows a depiction in tabular format of a data record embodiment created from using a structured testing method on the collection device of FIG. 3 according to the present invention.

DETAILED DESCRIPTION

Figure 1:
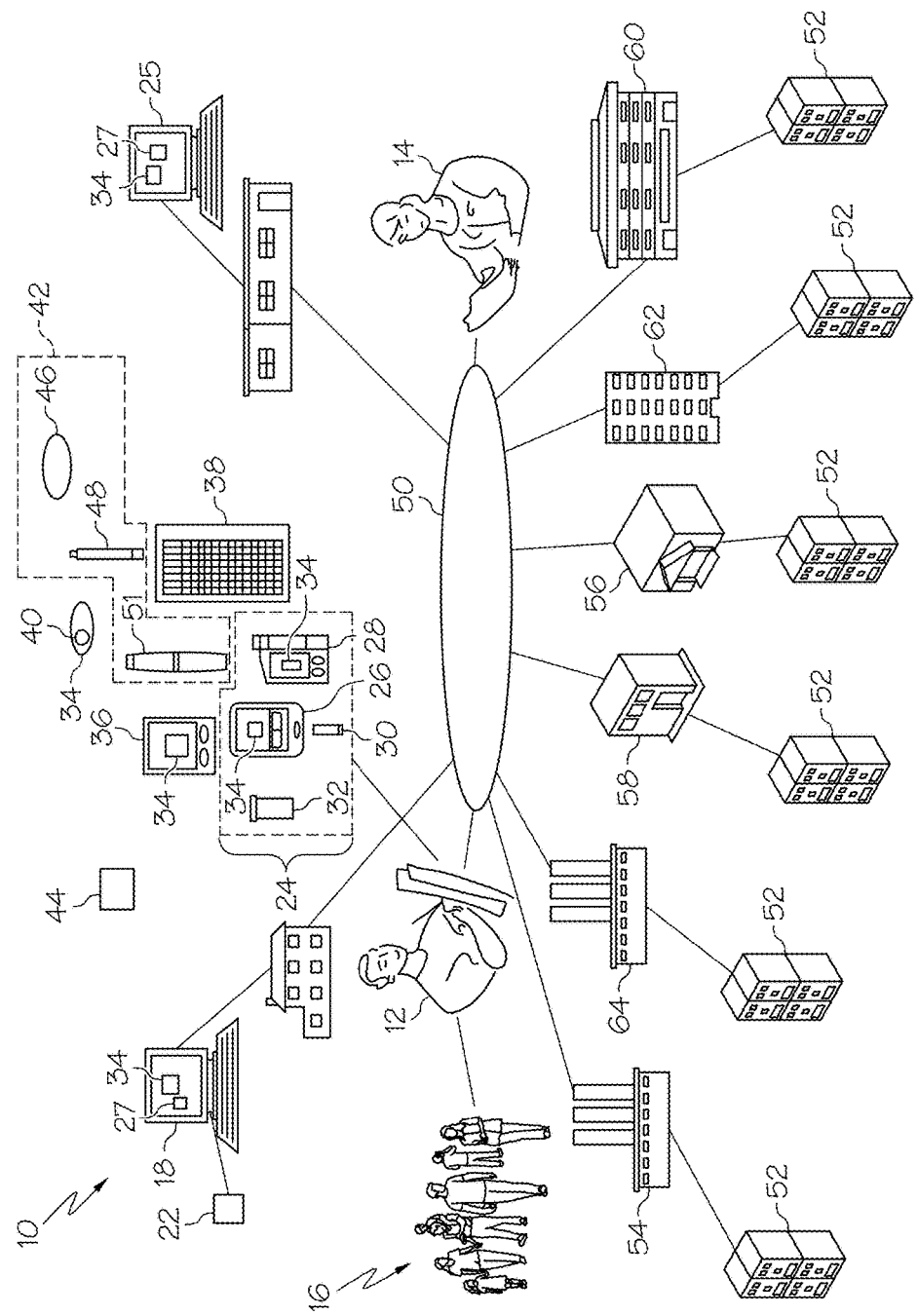
FIG. 1 is a diagram showing a chronic care management system for a diabetes patient and a clinician along with others having an interest in the chronic care management of the patient according to an embodiment of the present invention.

The present invention will be described below relative to various illustrative embodiments. Those skilled in the art will appreciate that the present invention may be implemented in a number of different applications and embodiments and is not specifically limited in its application to the particular embodiments depicted herein. In particular, the present invention will be discussed below in connection with diabetes management via sampling blood, although those of ordinary skill will recognize that the present invention could be modified to be used with other types of fluids or analytes besides glucose, and/or useful in managing other chronic diseases besides diabetes.

As used herein with the various illustrated embodiments described below, the follow terms include, but are not limited to, the following meanings.

The term "biomarker" can mean a physiological variable measured to provide data relevant to a patient such as for example, a blood glucose value, an interstitial glucose value, an HbA1c value, a heart rate measurement, a blood pressure measurement, lipids, triglycerides, cholesterol, and the like.

The term "contextualizing" can mean documenting and interrelating conditions that exists or will occur surrounding a collection of a specific biomarker measurement. Preferably, data about documenting and interrelating conditions that exists or will occur surrounding a collection of a specific biomarker are stored together with the collected biomarker data and are linked to it. In particular, a further assessment of the collected biomarker data takes into account the data about documenting and interrelating conditions so that not only the data as such are evaluated but also the link between data to which it is contextualized. The data about documenting and interrelating conditions can include for example information about the time, food and/or exercises which occurs surrounding a collection of a specific biomarker measurement and/or simultaneously thereto. For example, the context of a structured collection procedure according in an embodiment to the present invention can be documented by utilizing entry criterion for verifying a fasting state with the diabetic person before accepting a biomarker value during a Basal titration optimization focused testing procedure.

The term "criteria" can mean one or more criterions, and can be at least one or more of a guideline(s), rule(s), characteristic(s), and dimension(s) used to judge whether one or more conditions are satisfied or met to begin, accept, and/or end one or more procedural steps, actions, and/or values.

The term "adherence" can mean that a person following a structured collection procedure or a diabetes treatment protocol performs requested procedural steps appropriately. For example, the biomarker data should be measured under prescribed conditions of the structured collection procedure. If then the prescribed conditions are given for a biomarker measurement the adherence is defined as appropriate. For examples, the prescribed conditions are time related conditions and/or exemplarily can include eating of meals, taking a fasting sample, eating a type of meal with a requested window of time, taking a fasting sample at a requested time, sleeping a minimum amount of time, and the like. The adherence can be defined as appropriate or not appropriate for a structured collection procedure, a group of sample instances, or a single data point of a contextualized biomarker data. Preferably, the adherence can be defined as appropriate or not appropriate by a range of a prescribed condition(s) or by a selectively determined prescribed condition(s). Moreover the adherence can be calculated as a rate of adherence describing in which extent the adherence is given for a structured collection procedure or a single data point in particular of a contextualized biomarker data.

The term "medical use case or question" can mean at least one or more of a procedure, situation, condition, and/or question providing an uncertainty about the factuality of existence of some medical facts, combined with a concept that is not yet verified but that if true would explain certain facts or phenomena. Medical use case or question can be already deposited and stored in the system so that the diabetic person can select between different medical use cases or questions. Alternatively, the medical use case or question can be defined by the diabetic person themselves.

The terms "focused", "structured", and "episodic" are used herein interchangeably with the term "testing" and can mean a predefined sequence in which to conduct the testing.

The terms "diabetes treatment protocol" and "structured testing" may be used interchangeably herein to describe a sequence of tasks used in diabetes treatment or the optimization of diabetes treatment.

The terms "software" and "program" may be used interchangeably herein.

For example, the skill assessment permits the process 700 to check and assess if the individual possesses the proper level of skill before moving into a new activity and/or protocol, i.e., a different collection procedure 70. If not, then the process 700 then provides/recommends the skill development activities for the individual 12 to complete in order to gain the necessary skill level for the new activity and/or collection procedure 70.

FIG. 1 shows a chronic care management system 10 for a diabetes patient(s) 12 and a clinician(s) 14 along with others 16 having an interest in the chronic care management of the patient 12. Patient 12, having dysglycemia, may include persons with a metabolic syndrome, pre-diabetes, type 1 diabetes, type 2 diabetes, and gestational diabetes. The others 16 with an interest in the patient's care may include family members, friends, support groups, and religious organizations all of which can influence the patient's conformance with therapy. The patient 12 may have access to a patient computer 18, such as a home computer, which can connect to a public network 50 (wired or wireless), such as the internet, cellular network, etc., and couple to a dongle, docking station, or device reader 22 for communicating with an external portable device, such as a portable collection device 24. An example of a device reader is shown in the manual "Accu-Chek® Smart Pix Device Reader Diabetic person's Manual" (2008) available from Roche Diagnostics.

The collection device 24 can be essentially any portable electronic device that can function as an acquisition mechanism for determining and storing digitally a biomarker value(s) according to a structured collection procedure, and which can function to run the structured collection procedure and the method of the present invention. Greater details regarding various illustrated embodiments of the structured collection procedure are provided hereafter in later sections. In a preferred embodiment, the collection device 24 can be a self-monitoring blood glucose meter 26 or a continuous glucose monitor 28. An example of a blood glucose meter is the Accu-Chek® Active meter, and the Accu-Chek® Aviva meter described in the booklet "Accu-Chek® Aviva Blood Glucose Meter Owner's Booklet (2007)", portions of which are disclosed in U.S. Pat. No. 6,645,368 B1 entitled "Meter and method of using the meter for determining the concentration of a component of a fluid" assigned to Roche Diagnostics Operations, Inc., which is hereby incorporated by reference. An example of a continuous glucose monitor is shown in U.S. Pat. No. 7,389,133 "Method and device for continuous monitoring of the concentration of an analyte" (Jun. 17, 2008) assigned to Roche Diagnostics Operations, Inc., which is hereby incorporated by reference.

In addition to the collection device 24, the patient 12 can use a variety of products to manage his or her diabetes including: test strips 30 carried in a vial 32 for use in the collection device 24; software 34 which can operate on the patient computer 18, the collection device 24, a handheld computing device 36, such as a laptop computer, a personal digital assistant, and/or a mobile phone; and paper tools 38. Software 34 can be pre-loaded or provided either via a computer readable medium 40 or over the public network 50 and loaded for operation on the patient computer 18, the collection device 24, the clinician computer/office workstation 25, and the handheld computing device 36, if desired.

In still other embodiments, the software 34 can also be integrated into the device reader 22 that is coupled to the computer (e.g., computers 18 or 25) for operation thereon, or accessed remotely through the public network 50, such as from a server 52.

The patient 12 can also use for certain diabetes therapies, additional therapy devices 42, and other devices 44. Additionally, therapy devices 42 can include devices such as an ambulatory infusion pump 46, an insulin pen 48, and a lancing device 51. An example of an ambulatory insulin pump 46 include but not limited thereto the Accu-Chek® Spirit pump described in the manual "Accu-Chek® Spirit Insulin Pump System Pump Diabetic person Guide" (2007) available from Disetronic Medical Systems AG. The other devices 44 can be medical devices that provide patient data such as blood pressure, fitness devices that provide patient data such as exercise information, and elder care device that provide notification to care givers. The other devices 44 can be configured to communicate with each other according to standards planned by Continua® Health Alliance. These therapy devices can be separate or integrated into the collection devices and data processing devices described herein.

The clinicians 14 for diabetes are diverse and can include e.g., nurses, nurse practitioners, physicians, endocrinologists, and other such health care providers. The clinician 14 typically has access to a clinician computer 25, such as a clinician office computer, which can also be provided with the software 34. A healthcare record system 27, such as Microsoft® HealthVault™ and Google™ Health, may also be used by the patient 12 and the clinician 14 on computers 18, 25 to exchange information via the public network 50 or via other network means (LANs, WANs, VPNs, etc.), and to store information such as collection data from the collection device 24, handheld collection device 36, blood glucose monitor 28, etc to an electronic medical record of the patient e.g., EMR 53 (FIG. 2A) which can be provided to and from computer 18, 25 and/or server 52.

Figure 2:
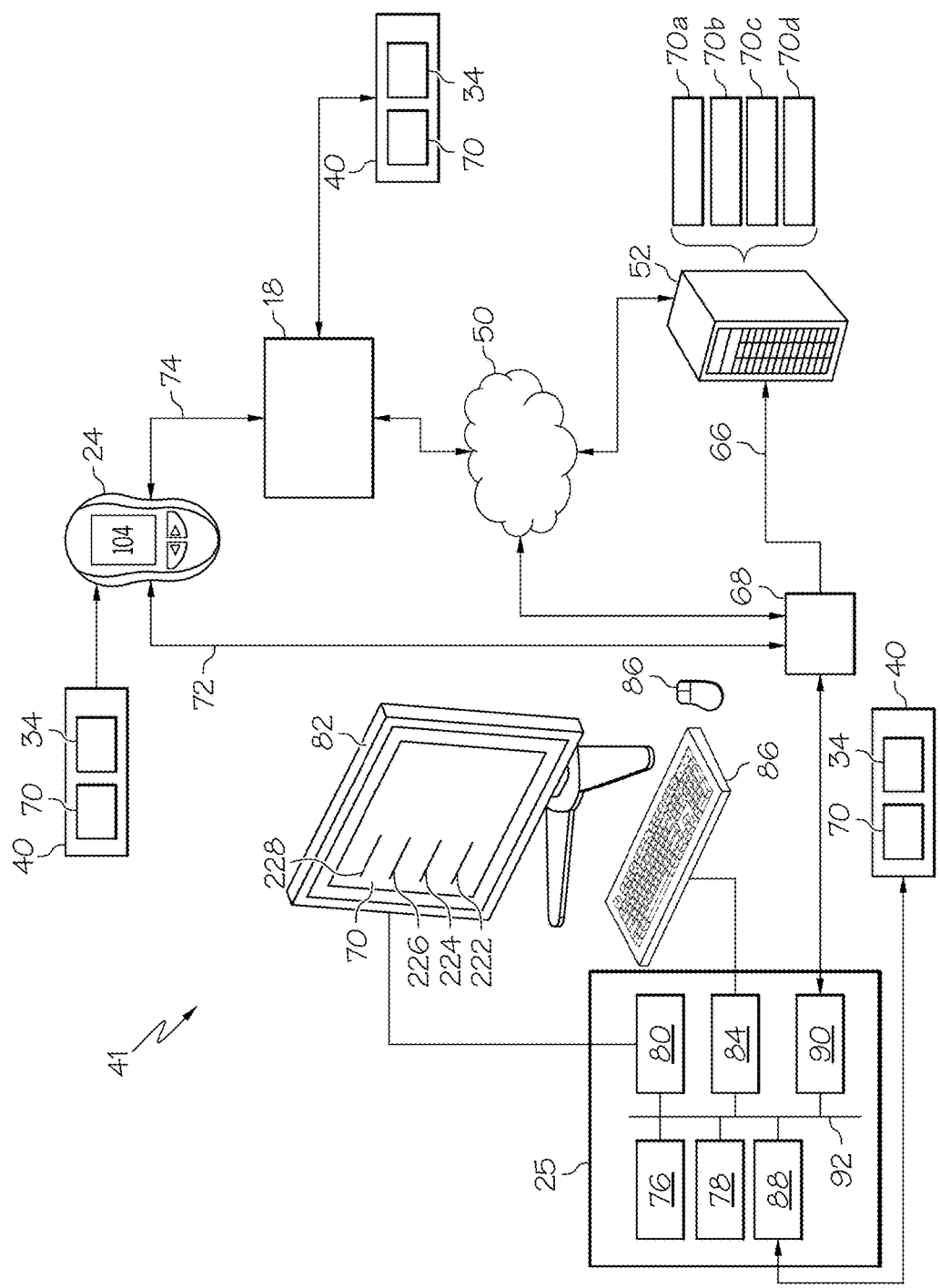
FIGS. 2 and 2A are diagrams showing embodiments of a system suitable for implementing a structured testing method according to an embodiment of the present invention.

Most patients 12 and clinicians 14 can interact over the public network 50 with each other and with others having computers/servers 52. Such others can include the patient's employer 54, a third party payer 56, such as an insurance company who pays some or all of the patient's healthcare expenses, a pharmacy 58 that dispenses certain diabetic consumable items, a hospital 60, a government agency 62, which can also be a payer, and companies 64 providing healthcare products and services for detection, prevention, diagnosis and treatment of diseases. The patient 12 can also grant permissions to access the patient's electronic health record to others, such as the employer 54, the payer 56, the pharmacy 58, the hospital 60, and the government agencies 62 via the healthcare record system 27, which can reside on the clinician computer 25 and/or one or more servers 52. Reference hereafter is also made to FIG. 2.

FIG. 2 shows a system embodiment suitable for implementing a structured testing method according to an embodiment of the present invention, which in another embodiment can be a part of the chronic care management system 10 and communicate with such components, via conventional wired or wireless communication means. The system 41 can include the clinician computer 25 that is in communication with a server 52 as well as the collection device 24. Communications between the clinician computer 25 and the server 52 can be facilitated via a communication link to the public network 50, to a private network 66, or combinations thereof. The private network 66 can be a local area network or a wide are network (wired or wireless) connecting to the public network 50 via a network device 68 such as a (web) server, router, modem, hub, and the likes.

In one embodiment, the server 52 can be a central repository for a plurality of structured collection procedures (or protocols) 70*a*, 70*b*, 70*c*, 70*d*, in which the details of a few exemplary structured collection procedures are provided in later sections. The server 52, as well as the network device 68, can function also as a data aggregator for completed ones of the structured collection procedures 70*a*, 70*b*, 70*c*, 70*d*. Accordingly, in such an embodiment, data of a completed collection procedure(s) from a collection device of the patient 12 can then be provided from the server 52 and/or network device 68 to the clinician computer 25 when requested in response to retrieval for such patient data.

Figure 2A:
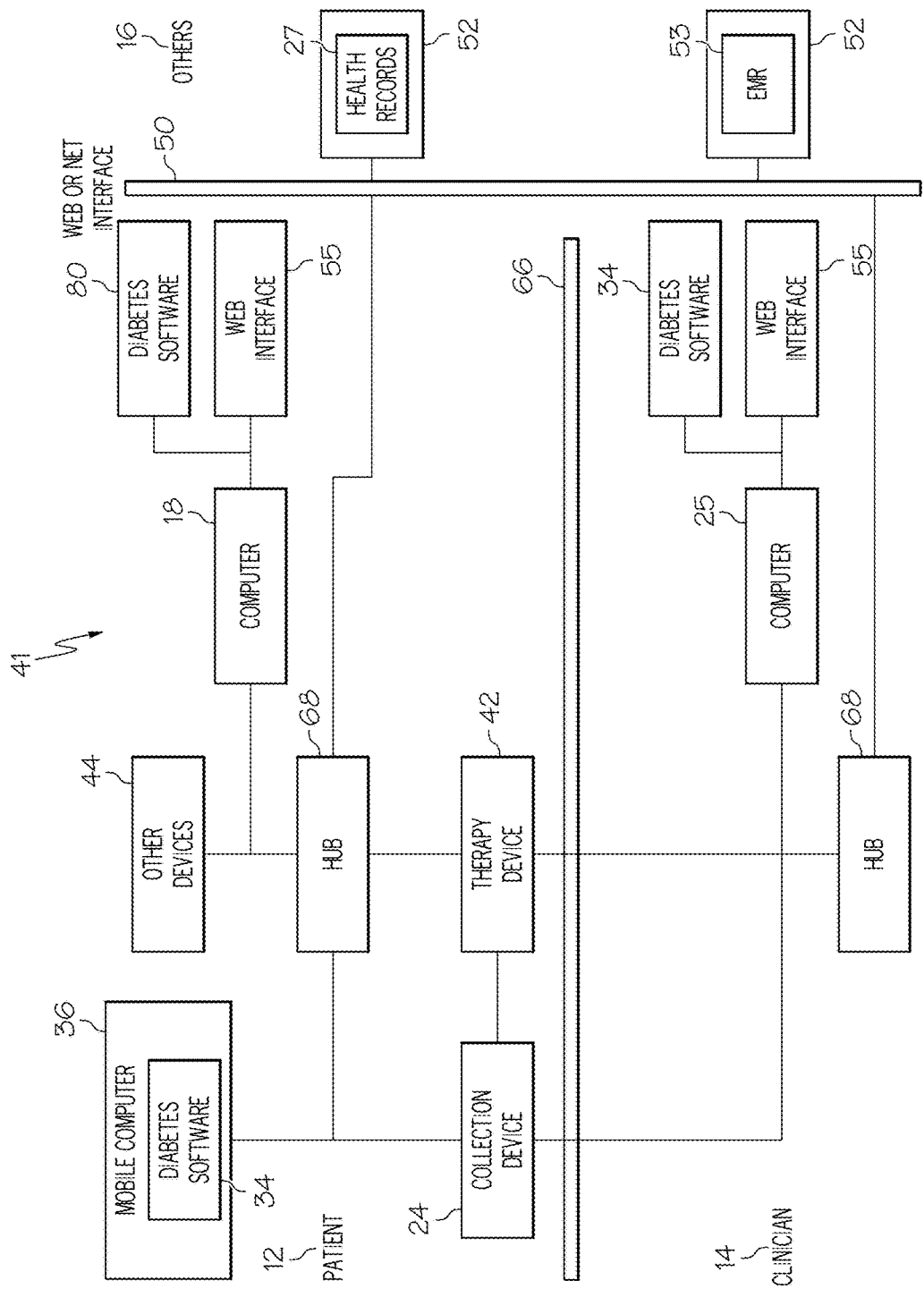

In one embodiment, one or more of the plurality of structured collection procedures 70*a*, 70*b*, 70*c*, 70*d* on the server 52 can be provided over the public network 50, such as through a secure web interface 55 (FIG. 2A, showing another embodiment of the system 41) implemented on the patient computer 18, the clinician computer 25, and/or the collection device 24. In another embodiment, the clinician computer 25 can serve as the interface (wired or wireless) 72 between the server 52 and the collection device 24. In still another embodiment, the structured collection procedures 70*a*, 70*b*, 70*c*, 70*d*, as well as software 34, may be provided on a computer readable medium 40 and loaded directed on the patient computer 18, the clinician computer 25, and/or the collection device 24. In still another embodiment, the structured collection procedures 70*a*, 70*b*, 70*c*, 70*d* may be provided pre-loaded (embedded) in the memory of the collection device 24. In still other embodiments, new/updated/modified structured collection procedures 70*a*, 70*b*, 70*c*, 70*d* may be sent between the patient computer 18, the clinician computer 25, the server 52 and/or the collection device 24 via the public network 50, the private network 66, via a direct device connection (wired or wireless) 74, or combinations thereof. Accordingly, in one embodiment the external devices e.g., computer 18 and 25, can be used to establish a communication link 72, 74 between the collection device 24 and still further electronic devices such as other remote Personal Computer (PC), and/or servers such as through the public network 50, such as the Internet and/or other communication networks (e.g., LANs, WANs, VPNs, etc.), such as private network 66.

Figure 3:
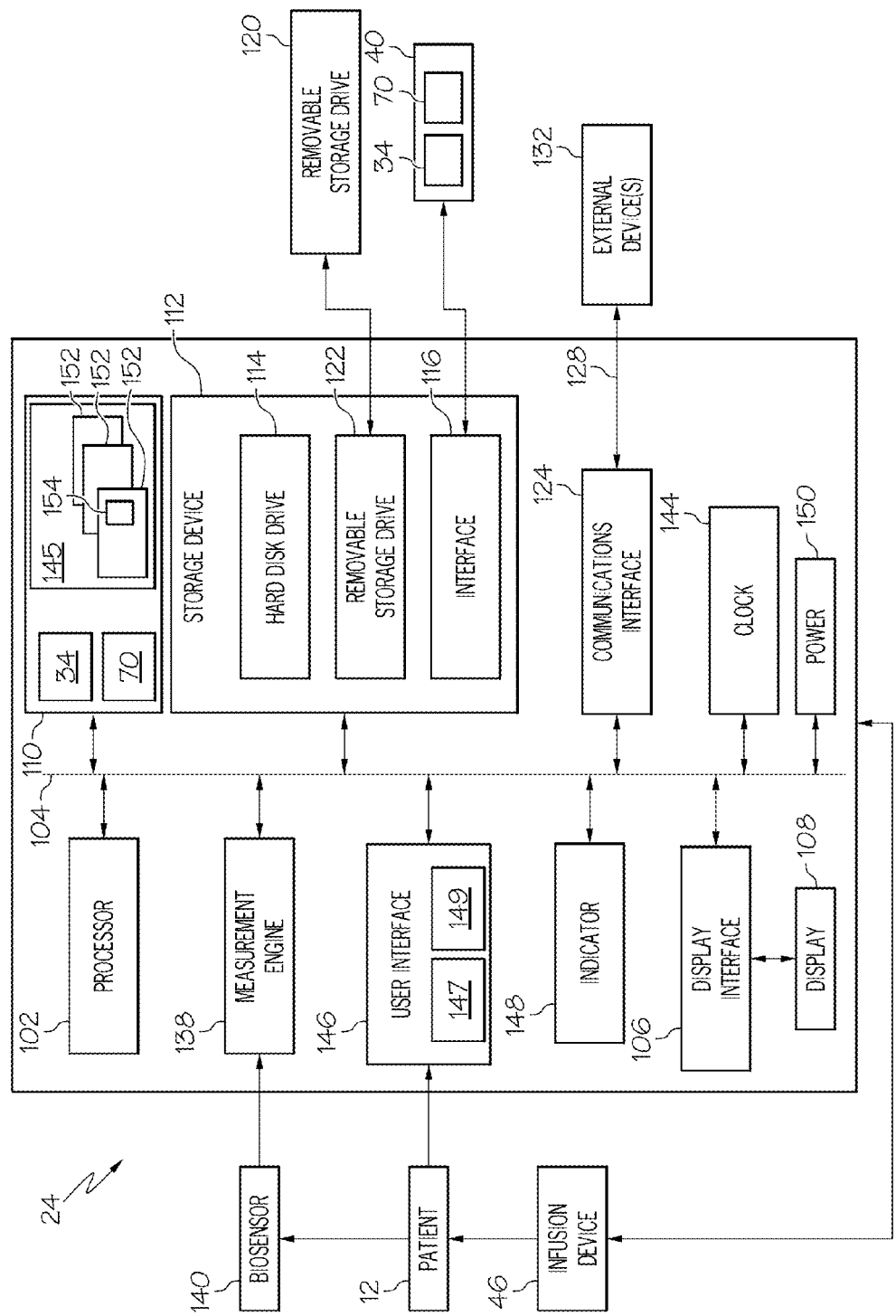
FIG. 3 shows a block diagram of a collection device embodiment according to the present invention.

The clinician computer 25, as a conventional personal computer/workstation, can include a processor 76 which executes programs, such as software 34, and such as from memory 78 and/or computer readable medium 40. Memory 78 can include system memory (RAM, ROM, EEPROM, etc.), and storage memory, such as hard drives and/or flash memory (internal or external). The clinician computer 25 can also include a display driver 80 to interface a display 82 with the processor 76, input/output connections 84 for connecting diabetic person interface devices 86, such as a keyboard and mouse (wired or wireless), and computer readable drives 88 for portable memory and discs, such as computer readable medium 40. The clinician computer 25 can further include communication interfaces 90 for connections to the public network 50 and other devices, such as collection device 24 (wired or wireless), and a bus interface 92 for connecting the above mentioned electronic components to the processor 76. Reference hereafter is now made to FIG. 3.

FIG. 3 is a block diagram conceptually illustrating the portable collection device 24 depicted in FIG. 2. In the illustrated embodiment, the collection device 24 can include one or more microprocessors, such as processor 102, which may be a central processing unit comprising at least one more single or multi-core and cache memory, which can be connected to a bus 104, which may include data, memory, control, and/or address buses. The collection device 24 can include the software 34, which provides instruction codes that causes a processor 102 of the device to implement the methods of the present invention that are discussed hereafter in later sections. The collection device 24 may include a display interface 106 providing graphics, text, and other data from the bus 104 (or from a frame buffer not shown) for display on a display 108. The display interface 106 may be a display driver of an integrated graphics solution that utilizes a portion of main memory 110 of the collection device 24, such as random access memory (RAM) and processing from the processor 102 or may be a dedicated graphic processing unit. In another embodiment, the display interface 106 and display 108 can additionally provide a touch screen interface for providing data to the collection device 24 in a well-known manner.

Main memory 110 in one embodiment can be random access memory (RAM), and in other embodiments may include other memory such as a ROM, PROM, EPROM or EEPROM, and combinations thereof. In one embodiment, the collection device 24 can include secondary memory 112, which may include, for example, a hard disk drive 114 and/or a computer readable medium drive 116 for the computer readable medium 40, representing for example, at least one of a floppy disk drive, a magnetic tape drive, an optical disk drive, a flash memory connector (e.g., USB connector, Firewire connector, PC card slot), etc. The drive 116 reads from and/or writes to the computer readable medium 40 in a well-known manner. Computer readable medium 40, represents a floppy disk, magnetic tape, optical disk (CD or DVD), flash drive, PC card, etc. which is read by and written to by the drive 116. As will be appreciated, the computer readable medium 40 can have stored therein the software 34 and/or structured collection procedures 70*a*, 70*b*, 70*c*, and 70*d* as well as data resulting from completed collections performed according to one or more of the collection procedures 70*a*, 70*b*, 70*c*, and 70*d*.

In alternative embodiments, secondary memory 112 may include other means for allowing the software 34, the collection procedures 70*a*, 70*b*, 70*c*, 70*d*, other computer programs or other instructions to be loaded into the collection device 24. Such means may include, for example, a removable storage unit 120 and an interface connector 122. Examples of such removable storage units/interfaces can include a program cartridge and cartridge interface, a removable memory chip (e.g., ROM, PROM, EPROM, EEPROM, etc.) and associated socket, and other removable storage units 120 (e.g. hard drives) and interface connector 122 which allow software and data to be transferred from the removable storage unit 120 to the collection device 24.

The collection device 24 in one embodiment can include a communication module 124. The communication module 124 allows software (e.g., the software 34, the collection procedures 70*a*, 70*b*, 70*c*, and 70*d*) and data (e.g., data resulting from completed collections performed according to one or more of the collection procedures 70*a*, 70*b*, 70*c*, and 70*d*) to be transferred between the collection device 24 and an external device(s) 126. Examples of communication module 124 may include one or more of a modem, a network interface (such as an Ethernet card), a communications port (e.g., USB, Firewire, serial, parallel, etc.), a PC or PCMCIA slot and card, a wireless transceiver, and combinations thereof. The external device(s) 126 can be the patient computer 18, the clinician computer 25, the handheld computing devices 36, such as a laptop computer, a personal digital assistance (PDA), a mobile (cellular) phone, and/or a dongle, a docking station, or device reader 22. In such an embodiment, the external device 126 may provided and/or connect to one or more of a modem, a network interface (such as an Ethernet card), a communications port (e.g., USB, Firewire, serial, parallel, etc.), a PCMCIA slot and card, a wireless transceiver, and combinations thereof for providing communication over the public network 50 or private network 66, such as with the clinician computer 25 or server 52. Software and data transferred via communication module 124 can be in the form of wired or wireless signals 128, which may be electronic, electromagnetic, optical, or other signals capable of being sent and received by communication module 124. For example, as is known, signals 128 may be sent between communication module 124 and the external device(s) 126 using wire or cable, fiber optics, a phone line, a cellular phone link, an RF link, an infrared link, other communications channels, and combinations thereof. Specific techniques for connecting electronic devices through wired and/or wireless connections (e.g. USB and Bluetooth, respectively) are well known in the art.

In another embodiment, the collection device 24 can be used with the external device 132, such as provided as a handheld computer or a mobile phone, to perform actions such as prompt a patient to take an action, acquire a data event, and perform calculations on information. An example of a collection device combined with such an external device 126 provided as a hand held computer is disclosed in U.S. patent application Ser. No. 11/424,757 filed Jun. 16, 2006 entitled "System and method for collecting patient information from which diabetes therapy may be determined," assigned to Roche Diagnostics Operations, Inc., which is hereby incorporated by reference. Another example of a handheld computer is shown in the diabetic person guide entitled "Accu-Chek® Pocket Compass Software with Bolus Calculator Diabetic person Guide" (2007) available from Roche Diagnostics.

In the illustrative embodiment, the collection device 24 can provide a measurement engine 138 for reading a biosensor 140. The biosensor 140, which in one embodiment is the disposable test strip 30 (FIG. 1), is used with the collection device 24 to receive a sample such as for example, of capillary blood, which is exposed to an enzymatic reaction and measured by electrochemistry techniques, optical techniques, or both by the measurement engine 138 to measure and provide a biomarker value, such as for example, a blood glucose level. An example of a disposable test strip and measurement engine is disclosed in U.S. Patent Pub. No. 2005/0016844 A1 "Reagent stripe for test strip" (Jan. 27, 2005), and assigned to Roche Diagnostics Operations, Inc., which is hereby incorporated by reference. In other embodiments, the measurement engine 138 and biosensor 140 can be of a type used to provide a biomarker value for other types of sampled fluids or analytes besides or in addition to glucose, heart rate, blood pressure measurement, and combinations thereof. Such an alternative embodiment is useful in embodiments where values from more then one biomarker type are requested by a structured collection procedure according to the present invention. In still another embodiment, the biosensor 140 may be a sensor with an indwelling catheter(s) or being a subcutaneous tissue fluid sampling device(s), such as when the collection device 24 is implemented as a continuous glucose monitor (CGM) in communication with an infusion device, such as pump 46 (FIG. 1). In still another embodiments, the collection device 24 can be a controller implementing the software 34 and communicating between the infusion device (e.g., ambulatory infusion pump 46 and electronic insulin pen 48) and the biosensor 140.

Data, comprising at least the information collected by the biosensor 140, is provided by the measurement engine 138 to the processor 102 which may execute a computer program stored in memory 110 to perform various calculations and processes using the data. For example, such a computer program is described by U.S. patent application Ser. No. 12/492,667, filed Jun. 26, 2009, titled "Method, System, and Computer Program Product for Providing Both an Estimated True Mean Blood Glucose Value and Estimated Glycated Hemoglobin (HbA1C) Value from Structured Spot Measurements Of Blood Glucose," and assigned to Roche Diagnostics Operations, Inc., which is hereby incorporated by reference. The data from the measurement engine 138 and the results of the calculation and processes by the processor 102 using the data is herein referred to as self-monitored data. The self-monitored data may include, but not limited thereto, the glucose values of a patient 12, the insulin dose values, the insulin types, and the parameter values used by processor 102 to calculate future glucose values, supplemental insulin doses, and carbohydrate supplement amounts as well as such values, doses, and amounts. Such data along with a date-time stamp 169 for each measured glucose value and administered insulin dose value is stored in a data file 145 of memory 110 and/or 112. An internal clock 144 of the collection device 24 can supply the current date and time to processor 102 for such use.

The collection device 24 can further provide a diabetic person interface 146, such as buttons, keys, a trackball, touchpad, touch screen, etc. for data entry, program control and navigation of selections, choices and data, making information requests, and the likes. In one embodiment, the diabetic person interface 146 can comprises one or more buttons 147, 149 for entry and navigation of the data provided in memory 110 and/or 112. In one embodiment, the diabetic person can use one or more of buttons 147, 149 to enter (document) contextualizing information, such as data related to the everyday lifestyle of the patient 12 and to acknowledge that prescribed tasks are completed. Such lifestyle data may relate to food intake, medication use, energy levels, exercise, sleep, general health conditions and overall well-being sense of the patient 12 (e.g., happy, sad, rested, stressed, tired, etc.). Such lifestyle data can be recorded into memory 110 and/or 112 of the collection device 24 as part of the self-monitored data via navigating through a selection menu displayed on display 108 using buttons 147, 149 and/or via a touch screen diabetic person interface provided by the display 108. It is to be appreciated that the diabetic person interface 146 can also be used to display on the display 108 the self monitored data or portions thereof, such as used by the processor 102 to display measured glucose levels as well as any entered data.

In one embodiment, the collection device 24 can be switched on by pressing any one of the buttons 147, 149 or any combination thereof. In another embodiment, in which the biosensor 140 is a test-strip, the collection device 24 can be automatically switched on when the test-strip is inserted into the collection device 24 for measurement by the measurement engine 138 of a glucose level in a sample of blood placed on the test-strip. In one embodiment, the collection device 24 can be switched off by holding down one of the buttons 147, 149 for a pre-defined period of time, or in another embodiment can be shut down automatically after a pre-defined period of non-use of the diabetic person interface 146.

An indicator 148 can also be connected to processor 102, and which can operate under the control of processor 102 to emit audible, tactile (vibrations), and/or visual alerts/reminders to the patient of daily times for bG measurements and events, such as for example, to take a meal, of possible future hypoglycemia, and the likes. A suitable power supply 150 is also provided to power the collection device 24 as is well known to make the device portable.

As mentioned above previously, the collection device 24 may be pre-loaded with the software 34 or by provided therewith via the computer readable medium 40 as well as received via the communication module 124 by signal 128 directly or indirectly though the external device 132 and/or network 50. When provided in the latter matter, the software 34 when received by the processor 102 of the collection device 24 is stored in main memory 110 (as illustrated) and/or secondary memory 112. The software 34 contains instructions, when executed by the processor 102, enables the processor to perform the features/functions of the present invention as discussed herein in later sections. In another embodiment, the software 34 may be stored in the computer readable medium 40 and loaded by the processor 102 into cache memory to cause the processor 102 to perform the features/functions of the invention as described herein. In another embodiment, the software 34 is implemented primarily in hardware logic using, for example, hardware components such as application specific integrated circuits (ASICs). Implementation of the hardware state machine to perform the feature/functions described herein will be apparent to persons skilled in the relevant art(s). In yet another embodiment, the invention is implemented using a combination of both hardware and software.

In an example software embodiment of the invention, the methods described hereafter can be implemented in the C++ programming language, but could be implemented in other programs such as, but not limited to, Visual Basic, C, C#, Java or other programs available to those skilled in the art. In still other embodiment, the program 34 may be implemented using a script language or other proprietary interpretable language used in conjunction with an interpreter. Reference hereafter is also made to FIG. 4.

FIG. 4 depicts in tabular form a data file 145 containing data records 152 of self-monitored data 154 resulting from a structured collection procedure according to an embodiment of the present invention. The data records 152 (e.g., rows) along with the self-monitoring data 154 (e.g., various one of the columns) can also provide associated therewith contextual information 156 (e.g., other various ones of the columns as well as via row and column header information). Such contextual information 156 can be collected either automatically, such as for example via input received automatically from the measurement engine, the biosensor, and/or any one of the other devices, or via input received from the diabetic person interface which was manually enter by the patient in response to a collection request (e.g., a question displayed by the processor 102 on the display 108) during the structured collection procedure. Accordingly, as such contextual information 156 can be provided with each data record 152 in a preferred embodiment, such information is readily available to a physician and no further collection of such information is necessarily needed to be provided again by the patient either manually or orally after completing the structured collection procedure. In another embodiment, if such contextual information 156 and/or additional contextual information is collected after completion of a structured collection procedure according to the present invention, such information may be provided in the associated data file and/or record 145, 152 at a later time such as via one of the computers 18, 25. Such information would then be associated with the self-monitored data in the data file 145, and thus would not need to be provided again orally or manually. Such a process in the latter embodiment may be needed in the situation where the structured collection procedure is implemented as or partly as a paper tool 38 which is used with a collection device incapable of running the software 34 implementing such a structured collection procedure.

It is to be appreciated that the date file 145 (or portions thereof, such as only the self-monitored data 154) can be sent/downloaded (wired or wireless) from the collection device 24 via the communication module 124 to another electronic device, such the external device 132 (PC, PDA, or cellular telephone), or via the network 50 to the clinician computer 25. Clinicians can use diabetes software provided on the clinician computer 25 to evaluate the received self-monitored data 154 as well as the contextual information 156 of the patient 12 for therapy results. An example of some of the functions which may be incorporated into the diabetes software and which is configured for a personal computer is the Accu-Chek® 360 Diabetes Management System available from Roche Diagnostics that is disclosed in U.S. patent application Ser. No. 11/999,968 filed Dec. 7, 2007, titled "METHOD AND SYSTEM FOR SETTING TIME BLOCK," and assigned to Roche Diagnostics Operations, Inc., which is hereby incorporated by reference.

In a preferred embodiment, the collection device 24 can be provided as portable blood glucose meter, which is used by the patient 12 for recording self-monitored data comprising insulin dosage readings and spot measured glucose levels. Examples of such bG meters as mentioned above previously include but are not limited to, the Accu-Chek® Active meter and the Accu-Chek® Aviva system both by Roche Diagnostics, Inc. which are compatible with the Accu-Chek® 360° Diabetes management software to download test results to a personal computer or the Accu-Chek® Pocket Compass Software for downloading and communication with a PDA. Accordingly, it is to be appreciated that the collection device 24 can include the software and hardware necessary to process, analyze and interpret the self monitored data in accordance with predefined flow sequences (as described below in detail) and generate an appropriate data interpretation output. In one embodiment, the results of the data analysis and interpretation performed upon the stored patient data by the collection device 24 can be displayed in the form of a report, trend-monitoring graphs, and charts to help patients manage their physiological condition and support patient-doctor communications. In other embodiments, the bG data from the collection device 24 may be used to generated reports (hardcopy or electronic) via the external device 132 and/or the patient computer 18 and/or the clinician computer 25.

The collection device 24 can further provide the diabetic person and/or his or her clinician with at least one or more of the possibilities comprising: a) editing data descriptions, e. g. the title and description of a record; b) saving records at a specified location, in particular in diabetic person-definable directories as described above; c) recalling records for display; d) searching records according to different criteria (date, time, title, description etc.); e) sorting records according to different criteria (e.g., values of the bG level, date, time, duration, title, description, etc.); f) deleting records; g) exporting records; and/or h) performing data comparisons, modifying records, excluding records as is well known.

As used herein, lifestyle can be described in general as a pattern in an individual's habits such as meals, exercise, and work schedule. The individual additionally may be on medications such as insulin therapy or orals that they are required to take in a periodic fashion. Influence of such action on glucose is implicitly considered by the present invention.

It is to be appreciated that the processor 102 of the collection device 24 can implement one or more structured collection procedures 70 provided in memory 110 and/or 112. Each structured collection procedure 70 in one embodiment can be stand-alone software, thereby providing the necessary program instructions which when executed by the processor 102 causes the processor to perform the structure collection procedure 70 as well as other prescribed functions. In other embodiments, each structured collection procedure 70 can be part of the software 34, and can be then be selectively executed by the processor 102 either via receiving a selection from a menu list provided in the display 108 from the diabetic person interface 146 in one embodiment or via activation of a particular diabetic person interface, such as a structured collection procedure run mode button (not shown) provided to the collection device 24 in another embodiment. It is to be appreciated that the software 34, likewise, provides the necessary program instructions which when executed by the processor 102 causes the processor to perform the structure collection procedure 70 as well as other prescribed functions of the software 34 discussed herein. One suitable example of having a selectable structured collection procedure provided as a selectable mode of a collection meter is disclosed by in U.S. patent application Ser. No. 12/491,523, filed Jun. 25, 2009, titled "Episodic Blood Glucose Monitoring System With An Interactive Graphical Diabetic person Interface And Methods Thereof," assigned to Roche Diagnostics Operations, Inc., which is hereby incorporated by reference.

In still another embodiment, a command instruction can be sent from the clinician computer 25 and received by the processor 102 via the communication module 124, which places the collection device 24 in a collection mode which runs automatically the structured collection procedure 70. Such a command instruction may specify which of the one or more structured collection procedures to run and/or provide a structured collection procedure to run. In still another embodiment, a list of defined medical use cases or medical questions can be presented on the display 108 by the processor 102, and a particular structured collection procedure 70 can be automatically chosen by the processor 102 from a plurality of structured collection procedures (e.g., procedures 70a, 70b, 70c, and 70d) depending on the selection of the defined medical use cases or medical questions received by the processor 102 via the diabetic person interface 146.

In still another embodiment, after selection, the structured collection procedure(s) 70 can be provided through the computer readable medium e.g., 40 and loaded by the collection device 24, downloaded from computer 18 or 25, the other device(s) 132, or server 52. Server 52, for example, may be a healthcare provider or company providing such pre-defined structured collection procedures 70 for downloading according to a selected defined medical use case or question. It is to be appreciated that the structured collection procedure(s) 70 may be developed by a healthcare company (e.g. company 64) and implemented via the public network 50 through a webpage and/or made available for downloading on server 52, such as illustrated in FIG. 2. In still other embodiments, notices that a new structured collection procedure 70 is available for use on the collection device 24 to help address a particular use case/medical question that a diabetic person (e.g., healthcare provider and patient) may have can be provided in any standard fashion, such for via postal letters/cards, email, text messaging, tweets, and the likes.

In some embodiments, as mentioned above previously, a paper tool 38 can perform some of the functions provided by the diabetes software 34. An example of some of the functions which may be incorporated into the diabetes software 34 and which is configured as a paper tool 38 is the Accu-Chek® 360 View Blood Glucose Analysis System paper form available from Roche Diagnostics also disclosed in U.S. patent application Ser. No. 12/040,458 filed Feb. 29, 2007 entitled "Device and method for assessing blood glucose control," assigned to Roche Diagnostic Operations, Inc., which is hereby incorporated by reference.

In still another embodiment, the software 34 can be implemented on the continuous glucose monitor 28 (FIG. 1). In this manner, the continuous glucose monitor 28 can be used to obtain time-resolved data. Such time-resolved data can be useful to identify fluctuations and trends that would otherwise go unnoticed with spot monitoring of blood glucose levels and standard HbA1c tests. Such as, for example, low overnight glucose levels, high blood glucose levels between meals, and early morning spikes in blood glucose levels as well as how diet and physical activity affect blood glucose along with the effect of therapy changes.

In addition to collection device 24 and software 34, clinicians 14 can prescribe other diabetes therapy devices for patients 12 such as an ambulatory insulin pump 46 as well as electronically based insulin pen 48 (FIG. 1). The insulin pump 46 typically includes configuration software such as that disclosed in the manual "Accu-Chek® Insulin Pump Configuration Software" also available from Disetronic Medical Systems AG. The insulin pump 46 can record and provide insulin dosage and other information, as well as the electronically based insulin pen 48, to a computer, and thus can be used as another means for providing biomarker data as requested by the structured collection procedure 70 (FIG. 2) according to the present invention.

It is to be appreciated that, and as mentioned above previously, one or more of the method steps discussed hereafter can be configured as a paper tool 38 (FIG. 1), but preferably all the method steps are facilitated electronically on system 41 (FIG. 2) or on any electronic device/computer, such as collection device 24, having a processor and memory as a program(s) residing in memory. As is known, when a computer executes the program, instructions codes of the program cause the processor of the computer to perform the method steps associated therewith. In still other embodiments, some or all of the method steps discussed hereafter can be configured on computer readable medium 40 storing instruction codes of a program that, when executed by a computer, cause the processor of the computer to perform the method steps associated therewith.

Before conducting the structured testing procedure of the diabetes treatment protocol, the present inventors recognized that it is beneficial to evaluate the complexity of the protocol in light of the skill level of the patient conducting the diabetes treatment protocol. Consequently, as shown in the embodiments of FIGS. 5A-5C, the present inventors have developed systems of tailoring the diabetes treatment to the proficiency level of the patient.

Figure 5A:
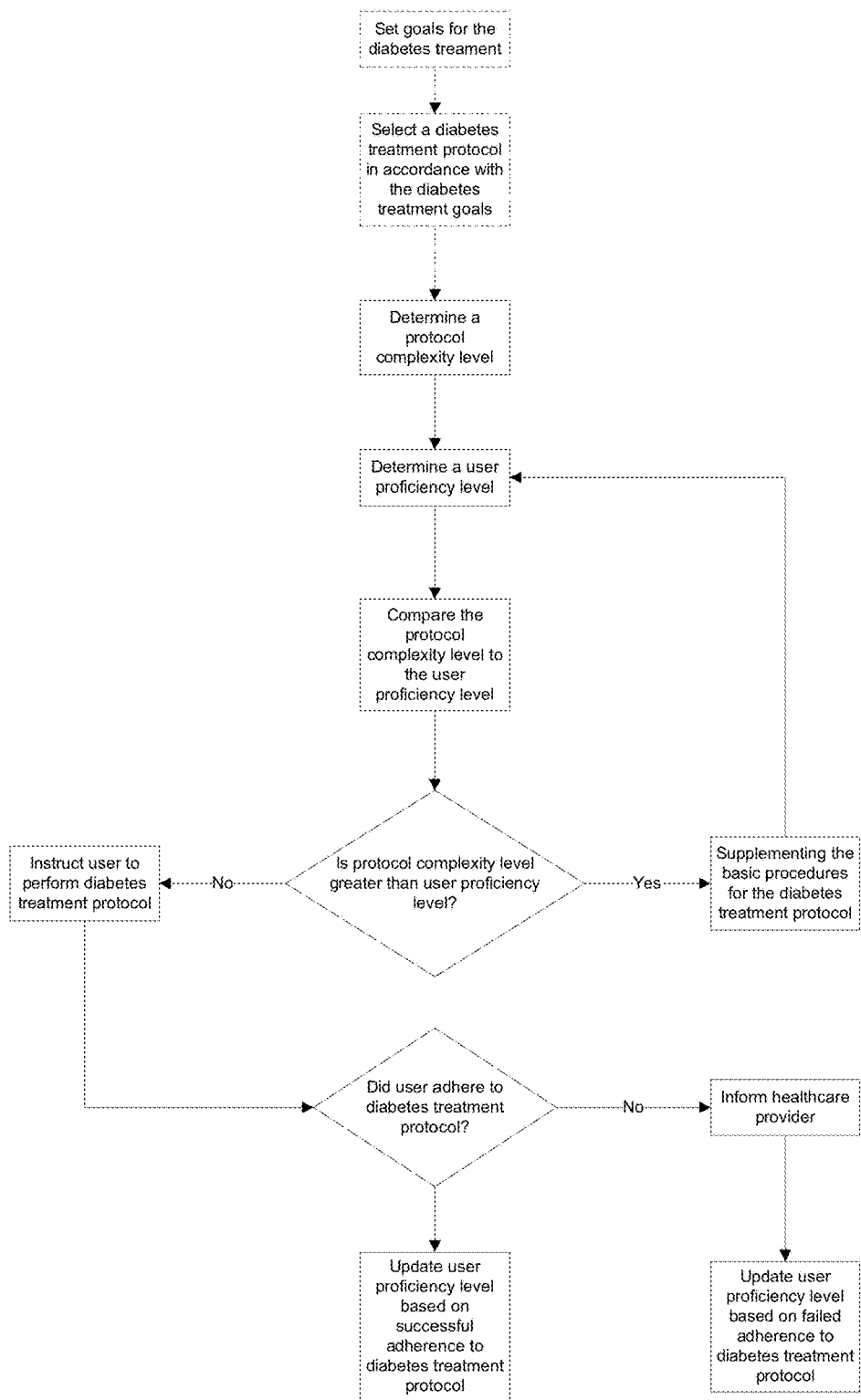
FIGS. 5A-5C are flow charts depicting various embodiments of tailoring the diabetes treatment protocol according to patient skill set.
Figure 5B:
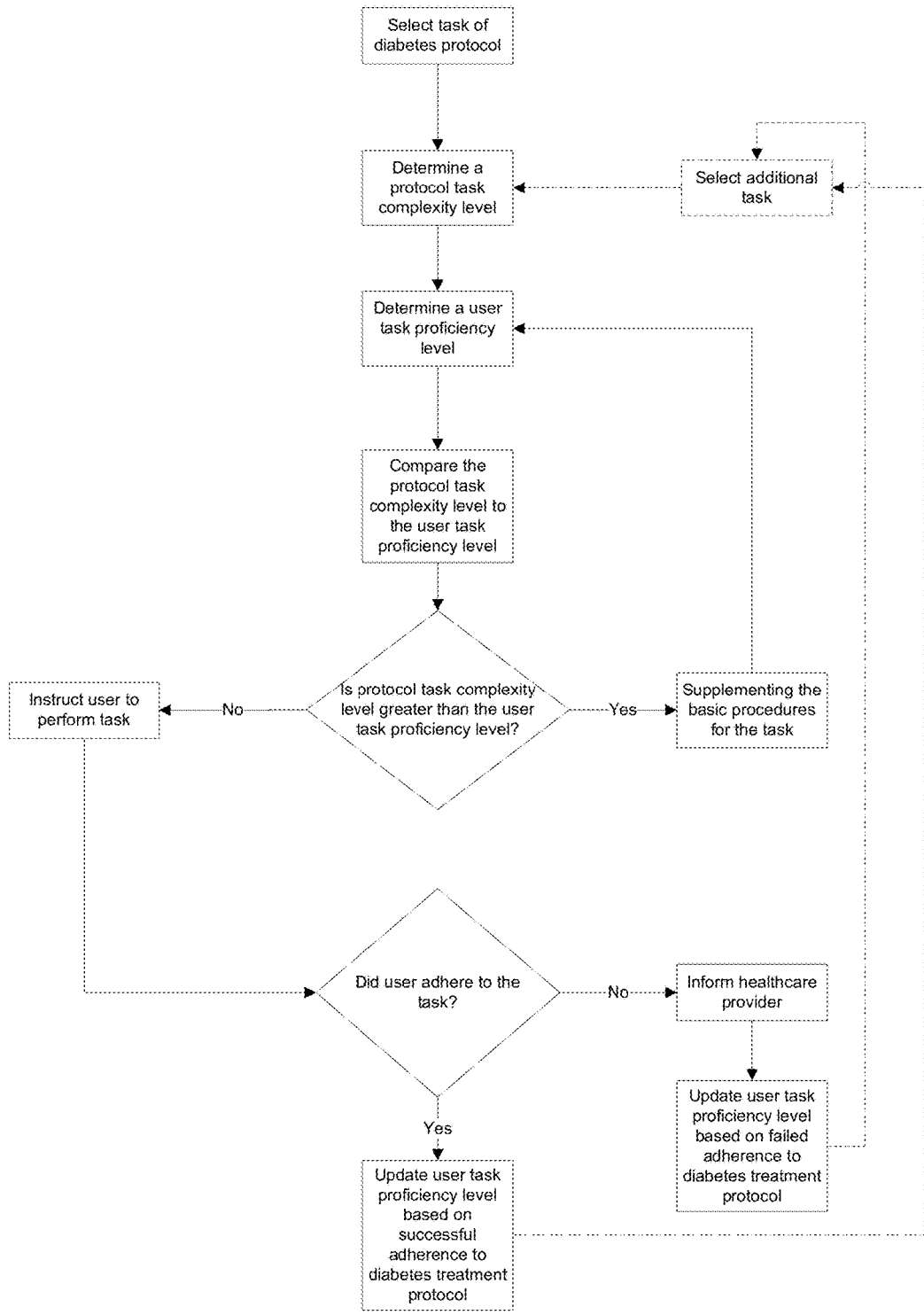
Figure 5C:
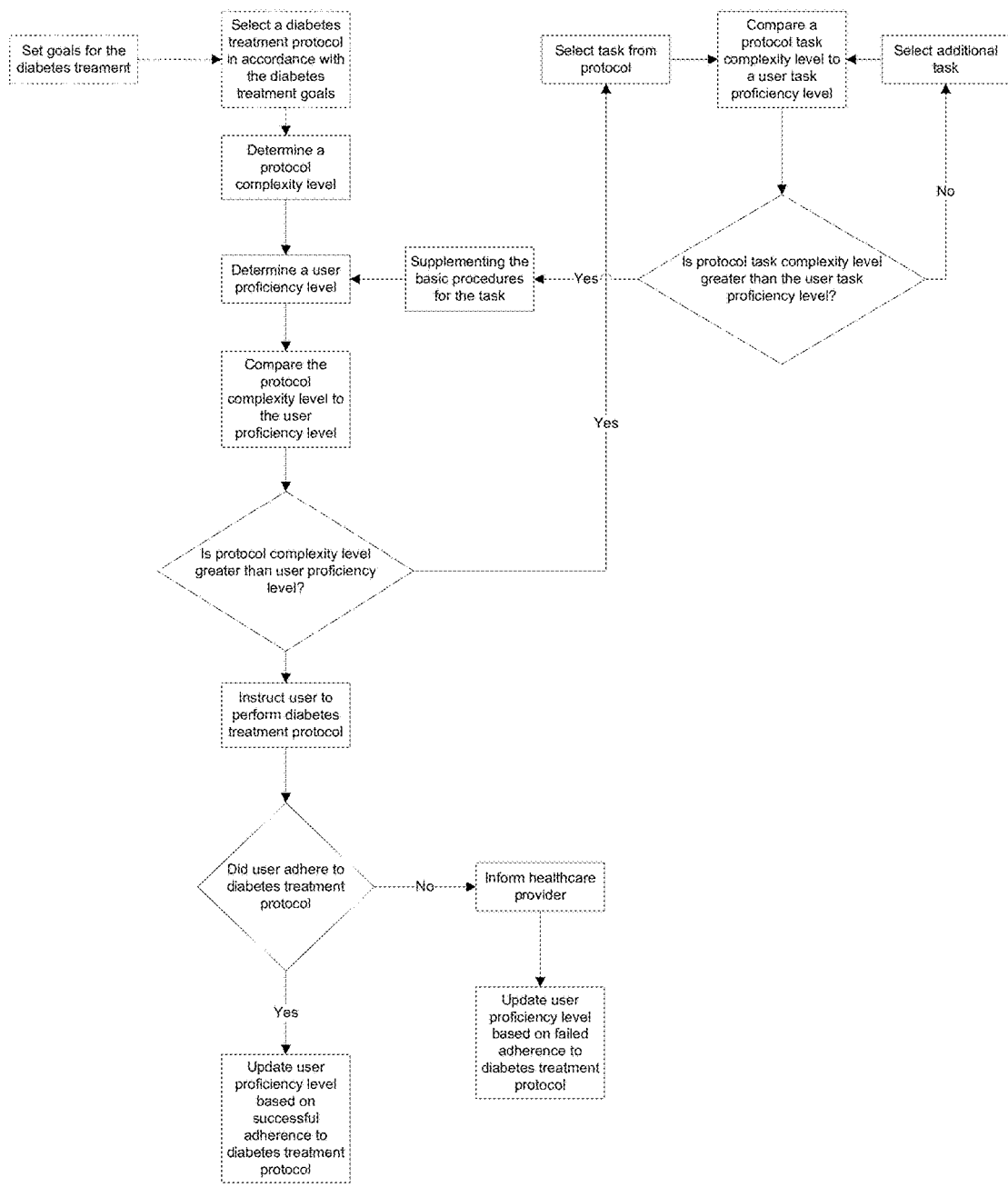

Referring to the embodiment of FIG. 5A, a method of tailoring a diabetes treatment protocol to a patient comprises determining a protocol complexity level corresponding to a degree of difficulty of completing a diabetes treatment protocol. As used herein, the diabetes treatment protocol comprises one or more tasks, and some procedures for performing the tasks of the diabetes treatment protocol. The tasks of the diabetes treatment protocol may be selected from the group consisting of obtaining biomarker readings, counting carbohydrate levels, administering insulin, are combinations thereof. The insulin may be basal or bolus insulin administered orally or via injection. The biomarker readings, which may be obtained after fasting, after a meal, after administration of insulin, or combinations thereof, may include information concerning a biomarker type selected from the group consisting of glucose, triglycerides, low density lipids, high density lipids, or combinations thereof.

The diabetes treatment protocol and the tasks of the diabetes treatment protocol are based on the treatment goals, for example, those treatment goals set by the healthcare provider. Based on the treatment goals, one or a plurality of diabetes treatment protocols may be developed, such that the patient or healthcare provider has the option to select the diabetes treatment protocol to be performed. Moreover, it enables the patient to understand the complexity of any task in the diabetes treatment protocol.

Embodiments of the disclosure can be implemented, for example, as follows: a paper tool; diabetes software integrated into a collection device such as a blood glucose meter; diabetes software integrated into a personal digital assistant, handheld computer, or mobile phone; diabetes software integrated into a device reader coupled to a computer; diabetes software operating on a computer such as a personal computer; and diabetes software accessed remotely through the internet. In collection devices, the display unit may provide one or more diabetes treatment protocols to the patient to facilitate the selection of a diabetes treatment protocol to be performed, wherein the selection may be performed by the patient of healthcare provider.

The protocol complexity level of the diabetes treatment protocol may be set by a healthcare provider, or may be calculated via the patient or a processor by utilizing various suitable metrics or guidelines. In one embodiment, the protocol complexity level may be calculated from rule based guidelines such as the Medication Regimen Complexity Index. These guidelines may be included in the software running on the collection device, or on a paper-based form or manual. Alternatively, empirically determined heuristics for task completion may be used to compute the protocol complexity level. For example, each task in the diabetes treatment protocol may be scored individually based on these empirically determined heuristics, and the protocol complexity level may then be calculated from the scores (i.e., the protocol task complexity levels as described in greater detail below) for all tasks in the diabetes treatment protocol. It is contemplated that the scores of each task may be weighted the same or differently. When computing the protocol complexity level, the protocol task complexity levels may be summed, averaged, or via another suitable mathematical operation. The protocol task levels and the protocol task complexity levels may be stored and used for subsequent analysis, for example, in the memory of a biomarker collection device.

In one embodiment, the method of calculating a protocol complexity level for the diabetes treatment protocol comprises selecting via the processor a calculation methodology for the protocol complexity level. Based on the diabetes treatment protocol and the tasks therein, the calculation instructions, which are programmed into the processor, enables the processor to select the calculation methodology which is appropriate for that diabetes treatment protocol. In one embodiment, the selected calculation methodology may calculate the protocol complexity level based on predefined or known diabetes protocol treatment complexity values associated with known diabetes treatment protocols. As some protocols have a known complexity value, the protocol complexity level may simply be this known value. In another embodiment, the selected calculation methodology may be computed from task complexity values for one or more tasks of the diabetes treatment protocol. These task complexity values may be weighted differently, weighted evenly, or it is possible that some tasks of the protocol may be ignored. For example, one task may greatly impact the complexity of the protocol, whereas another task is simplistic and does not add to the complexity of protocol, thus the complex task is weighted heavier in the computation of the protocol complexity level and the simplistic task is ignored.

In yet another embodiment, the calculation methodology may be computed from a combination of the predefined complexity values and the task complexity values for one or more tasks of the diabetes treatment protocol. In this calculation, the predefined diabetes protocol complexity values are weighted more, less or the same as the protocol task complexity levels in the calculation of the protocol complexity level. For example, the diabetes treatment protocol may comprise a known protocol plus an additional task. Thus, the protocol complexity calculation heavily weights the predefined diabetes protocol treatment but also considers the task complexity value of the additional task albeit at a lower weighting.

The complexity of a diabetes treatment protocol may depend on various factors associated with the diabetes treatment protocol. For example and not by way of limitation, these factors may include the frequency of insulin administration, a frequency of biomarker collection, the complexity of biomarker collection, a time of day of biomarker collection, a risk of adverse events associated with each task in the diabetes treatment protocol, and combinations thereof. Other factors like duration of the diabetes protocol may increase or decrease an overall complexity of the diabetes treatment protocol. In one exemplary embodiment, the patient is required to perform a task of administering the right dose of long-acting insulin at the right time, and also perform the task of collecting a biomarker reading (e.g., blood glucose) after fasting. Since these tasks are not complex (e.g., fasting bG in a morning time window), the weighting would not be as high as a corresponding blood glucose test within a narrower time window 2 hours after the consumption of a meal.

The protocol complexity level may be updated dynamically before, during and after the protocol. For example, if a task of the protocol is changed, added, or removed from the protocol, the processor may automatically recalculate the protocol complexity level upon the adjustment to the diabetes treatment protocol.

As an illustration, the protocol complexity level could be modeled on the ratings of ski/hiking trails (green circle to double black diamond). In such a mode, the envisioned difficulty of the set of structured tests would be divided into a fixed number of difficulty ratings (e.g., 4 or 5) and represented with a clearly distinguishable rating icon and possibly the associated numerical difficulty. In following with the ski trail theme, the least difficult rating (green circle 1) might be associated with a treatment protocol for collecting glucose measurements before and after breakfast, whereas the most difficult rating (double black diamond 5) might be associated with a treatment protocol intended to assess and optimize in a chained fashion the therapeutic parameters related to the basal rate, insulin-to-carbohydrate ratio, and insulin sensitivity factor for a patient on an insulin pump.

In addition to determining the protocol complexity level, the patient proficiency level is also determined, wherein the patient proficiency level corresponds to a skill set of the patient in conducting the diabetes treatment protocol. The patient proficiency level could be manually set by the healthcare provider. Alternatively, the proficiency level of individual tasks may be manually scored, and the patient proficiency level may be calculated from the manually scored patient task proficiency levels. The patient proficiency level may be determined based on a patient's answers to a survey, a patient's prior or current diabetes treatment regimen, or combinations thereof. The collection device may prompt the user with medical or treatment related questions to gather information to compute the patient proficiency level. Moreover, the patient proficiency level may also be computed from contextualized data associated with biomarker readings.

Additionally, like the protocol complexity level, the patient proficiency level may also be computed using a rule-based approach, or may also be computed based on the patient proficiency at individual tasks. In one embodiment, the patient proficiency level for a diabetes treatment protocol may be calculated by a processor programmed with calculation instructions for the patient proficiency level. These calculation instructions enable the processor to select a calculation methodology for the patient proficiency level which is appropriate for the diabetes treatment protocol. The selected calculation methodology may utilize predefined patient proficiency levels, the patient adherence level, the patient sophistication level, or various factors in its calculation of the patient proficiency level. In one example, the processor may determine whether a patient has previously performed the diabetes treatment protocol or any tasks of the diabetes treatment protocol, and thereby determine a patient adherence level for the performed diabetes treatment protocol or any performed tasks. Since the patient has conducted the protocol previously, the selected calculation methodology for the patient proficiency level may simply be computed from the patient adherence level, or may be computed from the patient proficiency level calculated for the previous protocol. If computed at a task level, the patient proficiency level may illustrate the progress of a patient during the diabetes treatment protocol.

In another embodiment, the patient proficiency levels may simply be calculated from predefined patient proficiency levels for known protocols. For example, it the patient proficiency level for a sample population conducting this protocol is known, that value may be used, typically as a starting point for the calculation of the patient proficiency level. If there is adherence data for the patient, than that data would be weighed more heavily in the calculation of the patient proficiency level than the predefined values.

Additionally, the selected calculation methodology may also consider a patient sophistication level. The patient sophistication level considers a patient's understanding and familiarity with how their body responds to specific actions. For example, a patient's understanding of how fasting, exercising, administering insulin, etc may affect their bG level provides an indication of the patient's effectiveness in a diabetes treatment protocol. As a result, the processor may evaluate the patient sophistication by comparing a patient estimate of their biomarker reading in comparison to a measured biomarker reading after a patient action, such as eating a meal, exercising, fasting, and administering insulin. This is called paired testing. If the estimate is close to the measured value, than the patient is deemed to be more sophisticated and their patient proficiency level may be raised accordingly. In addition to the above noted benefits, the embodiments of the present invention also enable self-discovery by the patient with diabetes. Self-discovery can accelerate learning by making concepts tangible and relevant to the patient. For example, by focusing on one specific event or activity, the patient is involved and has ownership in investigating what contributes to blood glucose (bG) spikes related to that specific event or activity. By focusing on one specific event or activity at a time, the patient may not be overwhelmed and the impact of a specific lifestyle choice on overall bG control can be isolated. In this manner, the patient can discover if a prescribed regimen works and determine for themselves whether a change in behavior is worthwhile. For example, patients with type 1 diabetes can use paired testing to understand how their body responds to different behaviors, like exercise, change in environment (e.g., going to camp, college, or work) or a change in routine (e.g., transition from a structured situation to the flexibility of holidays). Patients with type 2 diabetes are often asked to change multiple behaviors at once from food choices, portion sizes, exercise, etc., but the health impact is not always seen immediately. Paired testing links lifestyle to bG levels and thus reduces skepticism that a prescribed regime is worthwhile. Additionally, if the patient is receiving diabetes education, such as those with gestational diabetes, using the present invention to weave paired testing activates or events as explained hereafter into an education curriculum can help reinforce learning at each step and help link bG variation to daily lifestyle choices.

In addition, the selected calculation methodology may consider a patient's preferences when computing the patient proficiency level. For example, if a patient does not like to exercise, the patient will likely get a lower patient proficiency level for an exercise focused diabetes treatment protocol, or alternatively a higher patient proficiency level for a diabetes treatment protocol with minimal exercise focus. Consequently, the patient may be asked to select his or her most preferred activities, preferred food, behavior etc. If the diabetes treatment protocol can achieve the desired goals while including the patient preferences, this may increase the patient proficiency level and is a desirable outcome. If the diabetes treatment protocol does not include these patient preferences, the patient may be still be asked by the processor about the performance and/or adherence to the non-preferred tasks.

In addition to the above factors, the selected calculation methodology may also calculate the patient proficiency from a combination of the patient adherence level, the predefined patient proficiency levels, the patient sophistication level, and the patient preferences. Moreover, the patient proficiency level is dynamic and may be recalculated often, for example, upon successful completion of the diabetes protocol or individual tasks of the protocol, or upon the failure to complete the diabetes treatment protocol or the failure to complete individual tasks of the protocol. The user proficiency level may also be recalculated after changes to the diabetes treatment protocol.

Referring again to FIG. 5A, the methods of the present invention further comprise comparing the protocol complexity level to the patient proficiency level. If the patient proficiency level is at or above the protocol complexity level, then the procedures are deemed sufficient for the patient to perform the diabetes treatment protocol and the patient is instructed via the display unit to commence with the diabetes treatment protocol using the procedures. If the patient proficiency level is below the protocol complexity level, then the procedures should be supplemented to bridge the gap between the patient proficiency level and the protocol complexity level. The patient must possess the proper level of skill before moving onto a new task and/or protocol, i.e., a different collection procedure. If not, then the processor provides/recommends the skill development activities for the individual to complete in order to gain the necessary skill level for the new activity and/or collection procedure.

The supplemented procedures may comprise training materials, tutorials, additional instructions for one or more of the tasks of the diabetes treatment protocol, or combinations thereof. If the patient proficiency level is deficient because of the patient's inexperience with the protocol tasks, training or educational materials may be sufficient to enable the patient to improve his/her skill set, such that a patient proficiency level is on par with the protocol complexity level.

If the patient proficiency level is deficient because of the patient's prior lack of adherence to diabetes treatment protocols, the procedures may be supplemented with additional tools such as cognitive behavioral therapy or motivational interviewing. Additionally, the clinician might consider lower difficulty alternative structured tests to answer the medical question, or might consider offering intermediate communication with the patient to assess early any potential challenges. Moreover, the patient may be directed to exit the diabetes treatment protocol if the patient proficiency level is below the protocol complexity level.

Upon supplementation of the procedures, the patient may be instructed via the display unit to perform the tasks of the diabetes protocol using the supplemented procedures. Upon conducting the testing, it must be determined if the patient adheres to the diabetes treatment protocol. If the patient fails to adhere to the diabetes treatment protocol, the patient may be instructed via the display unit to contact a health care provider regarding the lack of adherence. In one embodiment, it may be possible for the patient to select a different diabetes treatment protocol if the patient proficiency level is below the protocol complexity level.

As an aid to the patient, the processor may automatically generate a status report based on the comparison of the protocol complexity level to the patient proficiency level. In addition to informing the patient or healthcare provider of the comparison, the status report may provide a probability of success for the patient in performing the diabetes treatment protocol, and subsequently may also automatically generate a status report when the patient has adhered or failed to adhere to the diabetes treatment protocol. If the probability of success is above a probability of success threshold value (for example, at least above 50% probability), the patient may then be instructed to perform the tasks of the diabetes treatment protocol. If the probability of success is below a threshold level, the procedures may be supplemented to increase the probability of success.

Status reporting of the structured collection procedure running on a device can be in printed and/or electronic format, and be provided to both patients and clinicians for different purposes, such as for the patient, e.g., troubleshooting, motivation, determining health status, the likes, and for the clinician, e.g., to learn about patients' needs, to identify depressive patients, to determine health status, and the like. Status reporting can be provided in many forms. For example, in certain structured collection procedure embodiments, information indicating at what stage of protocol execution that a patient is in can be provided. For example, a display can provide information e.g., such as in the form of a displayed electronic message. Additionally, results at the end of execution of the collection procedure can be provided to the patient in still other embodiments as part of a results message of the status reporting. In still other embodiments, a number of different reports can be electronically displayed as a report list, e.g., Report A, Report B, Report C, etc., from which a patient can select a desired report via the patient interface from the list at the conclusion of a structured collection procedure. In such an embodiment, for example, one report can be a tabular or a graphical representation of the outcome of the collection procedure. Another report can be a tabular or graphical representation of how well the collection procedure was followed, and still another report can be a tabular or graphical representation of performance on different aspects of the collection procedure to serve as a guide for selecting future collection procedures or identifying areas where additional patient support may be needed. Still other types of report may include: providing the number of adherence elements; providing the average glucose readings in fasting and in post-prandial periods; and providing the differences in bG in week and weekend periods. In still other embodiments, the functions of saving and printing a selected report can also be provided on the display by the device as well as transmitted to a designated health care provider via a send function. In such an embodiment, the health care provider can be designated in memory of the device such as by an email address and/or IP address, such as of a server, computer, and/or computing device of the health care provider, to which the selected report is sent, e.g. over network. In still other embodiments, the patient could be exposed to "partial" reporting of on-going results in anticipation of the reporting they would receive upon completion of the structured collection procedure. In further embodiments, such status reporting can be displayed on a number of different devices, such as the device reader, or with any other device including computer etc., that can display such status reporting of the collection procedure. For more details on status reporting, U.S. application Ser. No. 12/818,894 is incorporated by reference herein in its entirety.

As an alternative to considering the complexity of the entire protocol as shown in the embodiments of FIG. 5A, the embodiments of FIG. 5B facilitates the tailoring of individual tasks to a patient's skill set, such that a patient task proficiency level is at or above the complexity level of the individual task. In this embodiment, the protocol task complexity level is determined for at least one of the plurality of tasks of the diabetes treatment protocol, wherein the protocol task complexity level corresponds to a degree of difficulty of completing at least one of tasks in the diabetes treatment protocol. Similarly, the patient task proficiency level is also computed for the task, wherein the patient task proficiency level corresponds to a skill set of the patient in conducting the task. Both the protocol task complexity level and the patient task complexity level may be manually set, or may be computed via suitable guidelines or rules. If the patient task proficiency level is below the protocol complexity level, then the procedures are supplemented for at least the task at issue and the patient is instructed to perform one or more tasks of the diabetes treatment protocol. If the patient task proficiency level is above or at the protocol task complexity level, then the patient may be instructed via the display unit to perform the task; however, the procedures are not supplemented.

Referring to FIG. 5B, the patient's adherence to the task is also considered. If there has been adherence (e.g., the fasting blood glucose reading has been properly collected), the patient may be instructed to perform additional tasks in the diabetes treatment protocol. If the patient has failed to adhere to the task, the patient may be instructed to contact a health care provider. These steps may be repeated for any additional task in the diabetes treatment protocol.

Alternatively, the embodiment of FIG. 5C combines the protocol complexity level analysis as shown in FIG. 5A with the task specific complexity analysis as shown in FIG. 5B. This is advantageous, because it enables the patient or healthcare provider to pinpoint or troubleshoot any task in the diabetes treatment protocol which is causing a patient's skill set to be deficient in comparison to the protocol complexity level.

In the embodiment of FIG. 5C, the patient proficiency level is compared to the protocol complexity level. If the patient proficiency level is below the protocol complexity level, the complexity of at least one individual task should be considered. Referring again to FIG. 5C, the protocol task complexity level and a patient task proficiency level is then determined for at least one of the plurality of tasks of the diabetes treatment protocol. If the patient task proficiency level is below the protocol task complexity level for that task, the procedures may be supplemented for that individual task or for the protocol generally. If the patient task proficiency level is at or above the protocol task complexity level, other tasks should be evaluated in order to ascertain which task(s) has a protocol task complexity level greater than the patient task proficiency level, and is therefore driving a protocol complexity to a level higher than the patient proficiency level. By pinpointing individual tasks wherein the patient task proficiency level is below the protocol task complexity level, it is possible to bridge the knowledge gap for that deficient task and the protocol as a whole.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

All cited documents are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating diabetes of a patient comprising:
   collecting contextual information in response to responses received via a collection device prompting the patient with medical or treatment related questions before or during execution of a diabetes treatment protocol on the collection device;
   determining a protocol complexity level corresponding to a degree of difficulty of completing the diabetes treatment protocol by utilizing a processor;
   determining, based on the collected contextual information, a patient proficiency level corresponding to a skill set of the patient in conducting the diabetes treatment protocol by utilizing the processor;
   comparing the protocol complexity level to the patient proficiency level, wherein the comparison is performed by the processor; and
   subjecting the patient to a different diabetes treatment protocol executed on the collection device based on the comparison showing that the patient possesses a level of skill for the different diabetes treatment protocol, wherein the different diabetes treatment protocol comprises administering insulin to the patient.

2. The method of claim 1 further comprising supplementing procedures for performing the diabetes treatment protocol upon the comparison showing that the patient proficiency level is below the protocol complexity level.

3. The method of claim 2 wherein the supplemented procedures comprise training materials, tutorials, additional instructions for one or more of the tasks, or combinations thereof.

4. The method of claim 1 further comprising instructing the patient to exit the diabetes treatment protocol upon the comparison showing that the patient proficiency level is below the protocol complexity level.

5. The method of claim 1 further comprising automatically generating a status report based on the comparison of the protocol complexity level to the patient proficiency level.

6. The method of claim 5 wherein the status report provides a probability of success for the patient in performing the diabetes treatment protocol.

7. The method of claim 1 further comprising instructing the patient to perform tasks of the diabetes treatment protocol.

8. The method of claim 7 further comprising re-calculating the patient proficiency level after performing one or more of the tasks of the diabetes treatment protocol.

9. The method of claim 7 wherein one or more of the tasks of the diabetes treatment protocol are scored individually.

10. The method of claim 9 wherein the protocol complexity level is computed from the individual scores for the tasks in the diabetes treatment protocol.

11. The method of claim 1 further comprising determining whether the patient has adhered to the diabetes treatment protocol.

12. The method of claim 11 further comprising automatically generating a status report when the patient has failed to adhere to the diabetes treatment protocol.

13. The method of claim 11 further comprising instructing the patient to contact a health care provider upon the determination that the patient has failed to adhere to the diabetes treatment protocol.

14. The method of claim 1 wherein the patient proficiency level is further determined based on a patient's answers to a survey, a patient's prior or a current diabetes treatment regimen, or combinations thereof.

15. The method of claim 1 further comprising selecting another diabetes treatment protocol upon the comparison showing that the patient proficiency level is below the protocol complexity level for the diabetes treatment protocol during execution of the diabetes treatment protocol on the collection device.

16. The method of claim 1 further comprising setting diabetes treatment goals, and developing at least one diabetes treatment protocol in accordance with the diabetes treatment goals.

17. The method of claim 1 further comprising providing one or more diabetes treatment protocols to facilitate selection by the patient or healthcare provider of the diabetes treatment protocol to be performed.

18. The method of claim 1 comprising determining a protocol task complexity level for at least one task of the diabetes treatment protocol upon the comparison showing that the protocol complexity level is greater than the patient proficiency level of the diabetes treatment protocol, the protocol task complexity level corresponding to a degree of difficulty of completing at least one task in the diabetes treatment protocol;

determining a patient task proficiency level corresponding to the skill set of the patient in conducting at least one of the tasks of the diabetes treatment protocol; and comparing the protocol task complexity level to the patient task proficiency level.

19. The method of claim 18 further comprising selecting one or more different tasks of the diabetes treatment protocol upon the comparison showing that the patient task proficiency level is below the protocol task complexity level.

20. The method of claim 18 further comprising supplementing the procedures for that task upon the comparison showing that the patient task proficiency level is below the protocol task complexity level.

21. The method of claim 1, wherein the processor being programmed with calculation instructions for the protocol complexity level which corresponds to a degree of difficulty of completing the diabetes treatment protocol, the method further comprises:

selecting a calculation methodology for the protocol complexity level utilizing the processor, wherein the processor selects the calculation methodology appropriate for the diabetes treatment protocol by executing the programmed calculation instructions, wherein the selected calculation methodology utilizes
predefined protocol complexity values associated with known diabetes treatment protocols,
task complexity values which are assigned to one or more tasks of the diabetes treatment protocol, or combinations thereof; and
computing the protocol complexity level of the diabetes treatment protocol using the selected calculation methodology.

22. The method of claim 21 wherein the calculation methodology calculates the protocol complexity level by weighting task complexity values differently, weighting task values evenly, ignoring task complexity values for specific tasks, or combinations thereof.

23. The method of claim 21 further comprising adjusting the protocol complexity level upon determination that a duration of the diabetes treatment protocol or a number of steps of the diabetes treatment protocol increases or decreases an overall complexity of the diabetes treatment protocol.

24. The method of claim 21 wherein the protocol complexity level is calculated from the combination of predefined diabetes protocol complexity values and protocol task complexity level.

25. The method of claim 24 wherein predefined diabetes protocol complexity values are weighted more, less or the same as the protocol task complexity level in the calculation of the protocol complexity level.

26. The method of claim 24 wherein the protocol task complexity levels consider one or more factors selected from the group consisting of a frequency of insulin administration, a frequency of biomarker collection, the complexity of biomarker collection, a time of day of biomarker collection, a risk of adverse events associated with each task in the diabetes treatment protocol, and combinations thereof.

27. The method of claim 26 further comprising recalculating the protocol complexity level upon changes to the diabetes treatment protocol.

28. A collection device for supporting diabetes treatment of a patient, comprising:

a meter configured to measure one or more selected biomarkers;
a processor disposed inside the meter and coupled to memory,
software having instructions that when executed by the processor causes the processor to:
collect contextual information in response to responses received via prompts by the collection device to the patient with medical or treatment related questions before or during execution of a diabetes treatment protocol on the collection device;
compute a protocol complexity level corresponding to a degree of difficulty of completing the diabetes treatment protocol;
compute, based on the collected contextual information, a patient proficiency level corresponding to a skill set of the patient in conducting the diabetes treatment protocol;
compare the patient proficiency level and the protocol complexity level; and
execute on the collection device a different diabetes treatment protocol based on the comparison which shows that the patient possess a level of skill for the different diabetes treatment protocol, wherein the different diabetes treatment protocol comprises an administration of insulin to the patient; and
a display unit configured to provide the results of the comparison.

29. A collection device for supporting diabetes treatment of a patient, comprising:

a meter configured to measure one or more selected biomarkers;
a processor disposed inside the meter and coupled to memory;
software having instructions that when executed by the processor causes the processor to:
collect contextual information in response to responses received via prompts by the collection device to the patient with medical or treatment related questions before or during execution of a diabetes treatment protocol on the collection device;
select a calculation methodology appropriate for computing the protocol complexity level of the diabetes treatment protocol wherein the selected calculation methodology utilizes
predefined protocol complexity values associated with known diabetes treatment protocols, task complexity values which are assigned to one or more tasks of the diabetes treatment protocol, or combinations thereof;
compute the protocol complexity level corresponding to a degree of difficulty of completing of the diabetes treatment protocol;
compute, based on the collected contextual information, a patient proficiency level corresponding to a skill set of the patient in conducting the diabetes treatment protocol;
compare the patient proficiency level and the protocol complexity level; and
execute on the collection device a different diabetes treatment protocol based on the comparison which shows that the patient possess a level of skill for the different diabetes treatment protocol, wherein the different diabetes treatment protocol comprises an administration of insulin to the patient; and
a display unit configured to output the computed protocol complexity level.

* * * * *